US009460635B2

(12) United States Patent
Yu

(10) Patent No.: US 9,460,635 B2
(45) Date of Patent: Oct. 4, 2016

(54) OBSTACLE AVOIDANCE USING MOBILE DEVICES

(71) Applicant: AT&T Mobility II LLC, Atlanta, GA (US)

(72) Inventor: Loc Yu, Seattle, WA (US)

(73) Assignee: AT&T MOBILITY II LLC, Atlanta, GA (US)

( * ) Notice: Subject to any disclaimer, the term of this patent is extended or adjusted under 35 U.S.C. 154(b) by 399 days.

(21) Appl. No.: 14/019,567

(22) Filed: Sep. 6, 2013

(65) Prior Publication Data

US 2015/0070479 A1     Mar. 12, 2015

(51) Int. Cl.

| G09B 21/00 | (2006.01) |
|---|---|
| A45B 3/00 | (2006.01) |
| A45B 1/02 | (2006.01) |
| A45B 9/04 | (2006.01) |
| A61F 9/08 | (2006.01) |
| A45B 9/00 | (2006.01) |

(52) U.S. Cl.
CPC .............. *G09B 21/003* (2013.01); *A45B 1/02* (2013.01); *A45B 3/00* (2013.01); *A45B 9/04* (2013.01); *A45B 2009/002* (2013.01); *A61F 9/08* (2013.01)

(58) Field of Classification Search
CPC . G09B 21/003; A45B 1/02; A45B 2009/002
USPC .......................................................... 348/62
See application file for complete search history.

(56) References Cited

U.S. PATENT DOCUMENTS

| 6,044,165 | A | * | 3/2000 | Perona | G06K 9/222 |
|---|---|---|---|---|---|
| | | | | | 345/179 |
| 7,039,522 | B2 | | 5/2006 | Landau | |
| 7,230,538 | B2 | | 6/2007 | Lai et al. | |
| 7,388,516 | B2 | | 6/2008 | Yokota et al. | |
| 7,656,290 | B2 | | 2/2010 | Fein et al. | |
| 7,864,991 | B2 | | 1/2011 | Espenlaub et al. | |
| 8,331,628 | B2 | | 12/2012 | Stylianou et al. | |
| 2005/0060088 | A1 | | 3/2005 | Helal et al. | |
| 2006/0257137 | A1 | * | 11/2006 | Fromm | F16M 11/18 |
| | | | | | 396/420 |
| 2007/0085993 | A1 | | 4/2007 | Brown, Jr. | |
| 2007/0211947 | A1 | | 9/2007 | Tkacik | |
| 2008/0198222 | A1 | | 8/2008 | Gowda | |
| 2010/0263591 | A1 | * | 10/2010 | Nielsen | G06Q 10/06 |
| | | | | | 118/708 |
| 2011/0216179 | A1 | | 9/2011 | Dialameh et al. | |
| 2012/0327203 | A1 | | 12/2012 | Oh et al. | |
| 2013/0069862 | A1 | | 3/2013 | Ur | |
| 2013/0131985 | A1 | | 5/2013 | Weiland et al. | |
| 2013/0220392 | A1 | * | 8/2013 | Gassert | A61H 3/061 |
| | | | | | 135/66 |
| 2015/0084745 | A1 | * | 3/2015 | Hertz | H04W 4/02 |
| | | | | | 340/10.3 |

\* cited by examiner

*Primary Examiner* — Jessica M Prince
*Assistant Examiner* — Kathleen Nguyen
(74) *Attorney, Agent, or Firm* — Scott P. Zimmerman, PLLC

(57) ABSTRACT

Methods, systems, and products estimate distances to aid a visually impaired user of a mobile device. As the user carries the mobile device, a camera in the mobile device captures images of a walking cane. The images of the walking cane are analyzed to infer a distance between a tip of the walking cane and the mobile device. The distance may then used by navigational tools to aid the visually impaired user.

17 Claims, 28 Drawing Sheets

OBSTACLE AVOIDANCE USING MOBILE DEVICES

COPYRIGHT NOTIFICATION

A portion of the disclosure of this patent document and its attachments contain material which is subject to copyright protection. The copyright owner has no objection to the facsimile reproduction by anyone of the patent document or the patent disclosure, as it appears in the Patent and Trademark Office patent files or records, but otherwise reserves all copyrights whatsoever.

BACKGROUND

Avoiding obstacles is desirable for all people. Curbs, hydrants, poles, and other obstacles present safety concerns. These obstacles are especially hazardous to visually impaired people.

BRIEF DESCRIPTION OF THE SEVERAL VIEWS OF THE DRAWINGS

The features, aspects, and advantages of the exemplary embodiments are understood when the following Detailed Description is read with reference to the accompanying drawings, wherein.

DETAILED DESCRIPTION

The exemplary embodiments will now be described more fully hereinafter with reference to the accompanying drawings. The exemplary embodiments may, however, be embodied in many different forms and should not be construed as limited to the embodiments set forth herein. These embodiments are provided so that this disclosure will be thorough and complete and will fully convey the exemplary embodiments to those of ordinary skill in the art. Moreover, all statements herein reciting embodiments, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and the like represent conceptual views or processes illustrating the exemplary embodiments. The functions of the various elements shown in the figures may be provided through the use of dedicated hardware as well as hardware capable of executing associated software. Those of ordinary skill in the art further understand that the exemplary hardware, software, processes, methods, and/or operating systems described herein are for illustrative purposes and, thus, are not intended to be limited to any particular named manufacturer.

As used herein, the singular forms "a," "an," and "the" are intended to include the plural forms as well, unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

It will also be understood that, although the terms first, second, etc. may be used herein to describe various elements, these elements should not be limited by these terms. These terms are only used to distinguish one element from another. For example, a first device could be termed a second device, and, similarly, a second device could be termed a first device without departing from the teachings of the disclosure.

Figure 1:
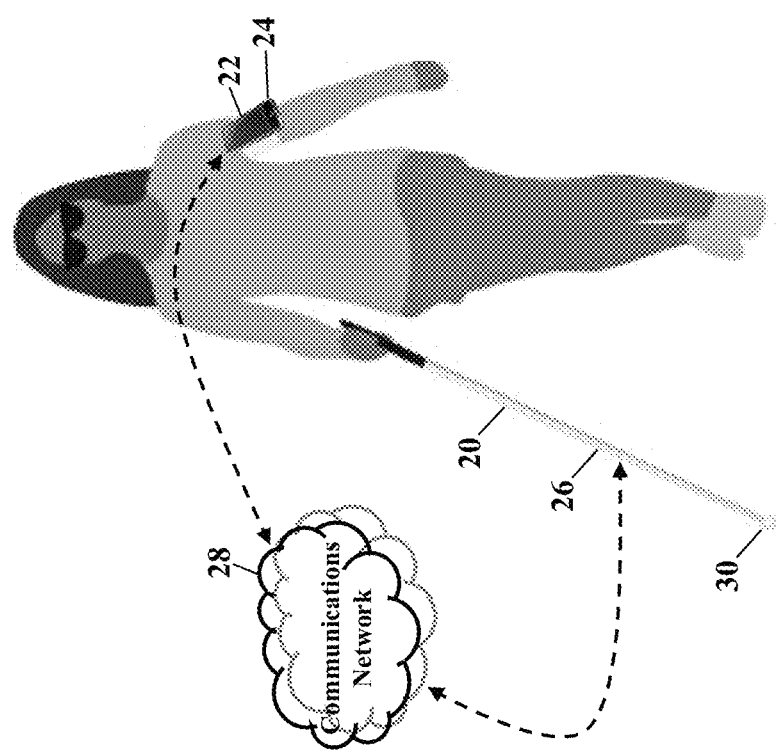
FIG. 1 is a simplified schematic illustrating an environment in which exemplary embodiments may be implemented.

FIG. 1 is a simplified schematic illustrating an environment in which exemplary embodiments may be implemented. FIG. 1 illustrates a walking cane 20 that electronically pairs with a mobile device 22. The mobile device 22, for simplicity, is illustrated as a smart phone 24 worn around an arm of a user. The mobile device 22, however, may be any processor-controlled device, as later paragraphs will explain. Electronic circuitry 26 allows the walking cane 20 to communicate with the mobile device 22 over a communications network 28. As a user carries the mobile device 22, the walking cane 20 and the mobile device 22 establish communication to help avoid obstacles in the user's path. For example, the walking cane 20 and the mobile device 22 cooperate to determine a location of a tip 30 of the walking cane 20. Once the location of the tip 30 is determined, the walking cane 20 and the mobile device 22 cooperate to infer distances to obstacles. The mobile device 22 may then generate audible warnings to alert the user of the obstacles. The mobile device 22 may even generate directions to avoid the obstacles.

Figure 2:
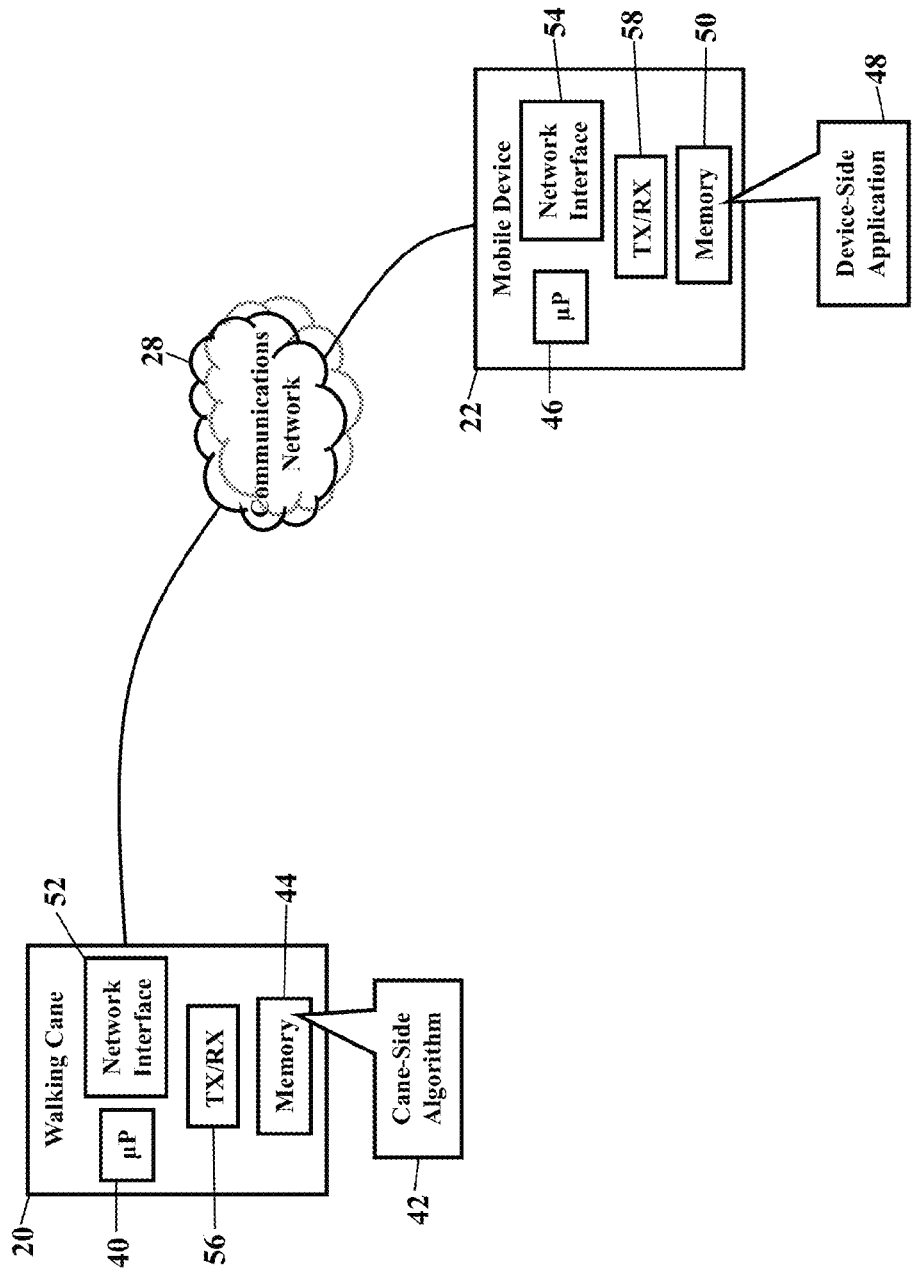
FIG. 2 is a more detailed schematic illustrating an operating environment, according to exemplary embodiments.
Figure 3:
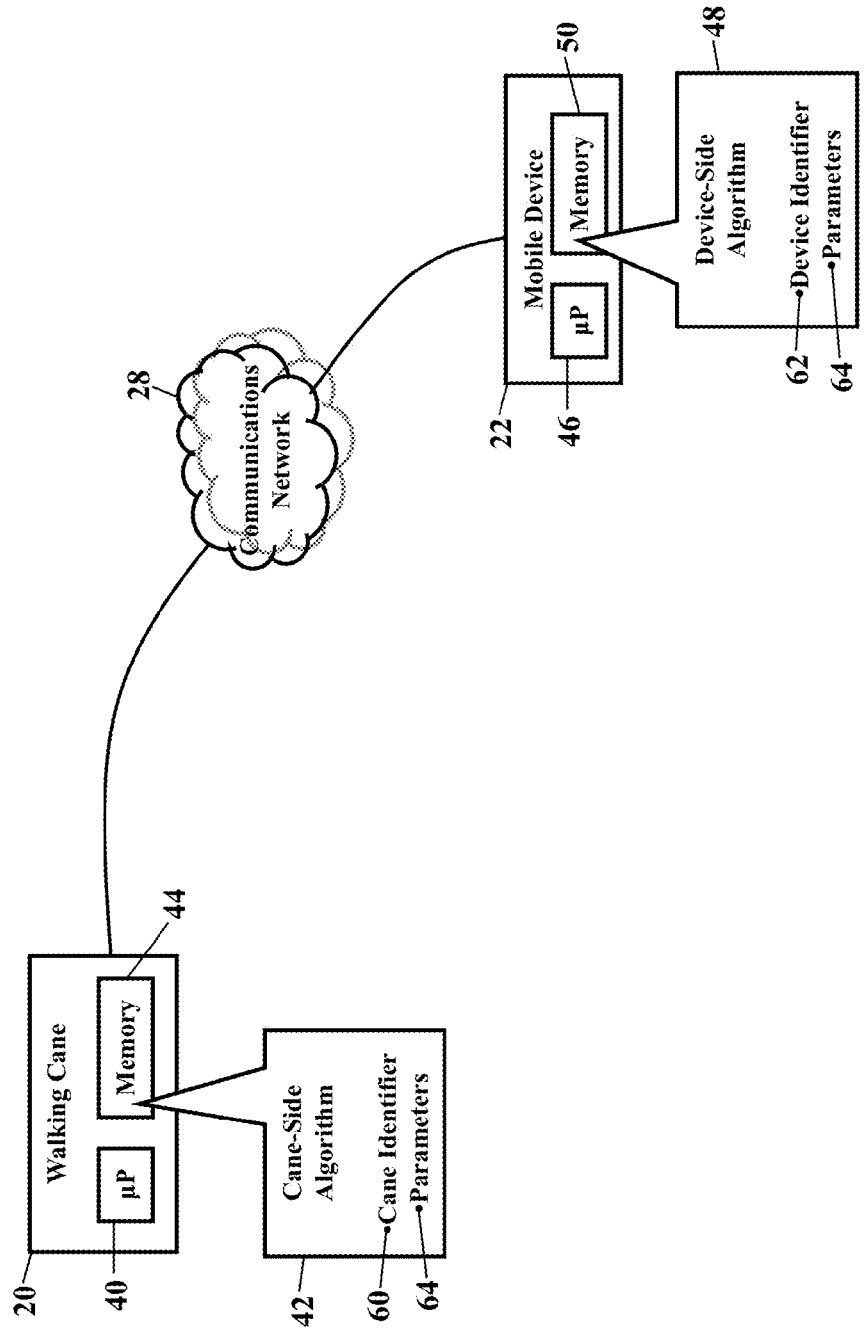
FIGS. 3-8 are schematics illustrating electronic pairing, according to exemplary embodiments.

FIG. 2 is a more detailed block diagram illustrating the operating environment, according to exemplary embodiments. The walking cane 20 may have a processor 40 (e.g., "μP"), application specific integrated circuit (ASIC), or other component that executes a cane-side algorithm 42 stored in a memory 44. The mobile device 22 may also have a processor 46 (e.g., "μP"), application specific integrated circuit (ASIC), or other component that executes a device-side algorithm 48 stored in memory 50. The cane-side algorithm 42 and/or the device-side algorithm 48 includes instructions, code, and/or programs that help avoid obstacles in the path of the walking cane 20 and/or the mobile device 22. Because the walking cane 20 and the mobile device 22 establish communication, the walking cane 20 has a cane network interface 52 to the communications network 28. The mobile device 22 also has a device network interface 54 to the communications network 28. The walking cane 20 and the mobile device 22 may each have transceivers 56 and 58 for transmitting and/or receiving signals.

Exemplary embodiments may be applied regardless of networking environment. Any networking technology may be used to establish communication between the walking cane 20 and the mobile device 22. The communications network 28, for example, may be a wireless network having cellular, WI-FI®, and/or BLUETOOTH® capability. The cane network interface xx and the device network interface xx may thus interface with the cellular, WI-FI®, and/or BLUETOOTH® communications network 28. The networking environment may utilize near-field (short distance) or far-field (long distance) techniques. The networking environment may operate using the radio-frequency domain and/or the Internet Protocol (IP) domain. The networking environment may even include a distributed computing network, such as the Internet (sometimes alternatively known as the "World Wide Web"), an intranet, a local-area network (LAN), and/or a wide-area network (WAN). The networking environment may include physical connections, such as USB cables, coaxial cables, copper wires, fiber optic lines, and/or hybrid-coaxial lines. Preferably, though, the communications network 28 and the network interface xx utilizes any portion of the electromagnetic spectrum and any signaling standard (such as the IEEE 802 family of standards, GSM/CDMA/TDMA or any cellular standard, and/or the ISM band). The concepts described herein may be applied to any wireless/wireline communications network, regardless of physical componentry, physical configuration, or communications standard(s).

FIGS. 3-8 are schematics illustrating electronic pairing, according to exemplary embodiments. Because the walking cane 20 and the mobile device 22 establish communication, the walking cane 20 and the mobile device 22 may have any registration or handshake procedure. The walking cane 20, for example, may use its transceiver (illustrated as reference numeral 56 in FIG. 2) to send or broadcast a cane identifier 60. The cane identifier 60 may be any alphanumeric combination that uniquely identifies the walking cane 20. The cane identifier 60, for example, may be an Internet Protocol address or a media access control ("MAC") address that uniquely identifies the walking cane 22 and/or the cane network interface (illustrated as reference numeral 42 in FIG. 2). The cane identifier 60, however, may be any other identification, such as a serial number, model number, name, or code. The mobile device 22, similarly, may use its transceiver (illustrated as reference numeral 58 in FIG. 2) to send or broadcast its unique device identifier 62. The device identifier 62 may be any alphanumeric combination, such as its corresponding Internet Protocol address, media access control ("MAC") address, serial number, model number, name, or code.

The walking cane 20 and the mobile device 22 electronically pair. Once either the cane identifier 60 or the device identifier 62 is retrieved, registration may be performed. Because the cane identifier 60 and the device identifier 62 are preferably uniquely assigned, the cane identifier 60 and/or the device identifier 62 may be used to retrieve parameters 64 for the pairing. These parameters 64 may then be used to perform calculations, as later paragraphs explain.

Figure 4:
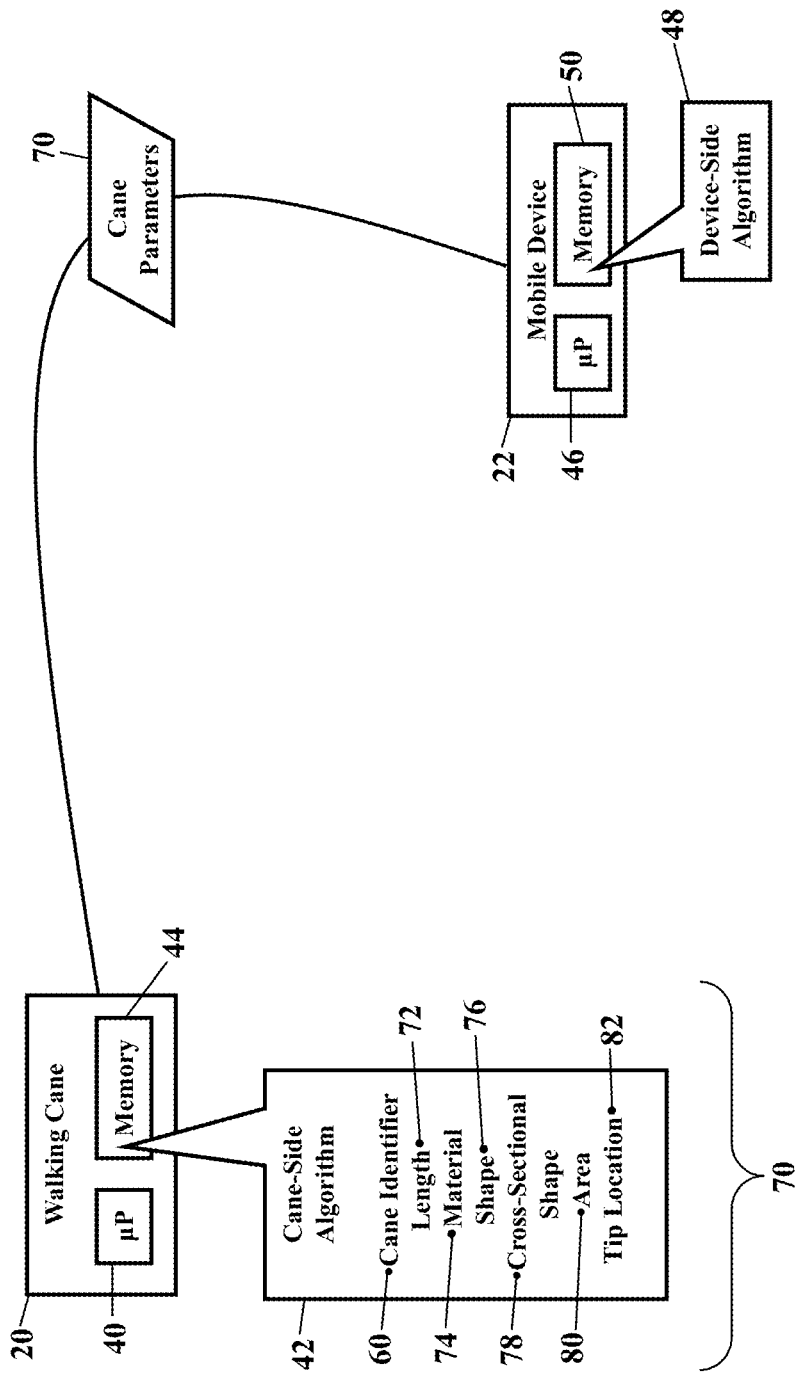

FIG. 4, for example, illustrates various cane parameters 70. The cane parameters 70 describe characteristics associated with the walking cane 20. FIG. 4 illustrates cane parameters 70 being locally stored in the memory 44 of the walking cane 20. During the electronic pairing operation, the walking cane 20 may retrieve any of the cane parameters 70 from the memory 44 and send the cane parameters 70 to the mobile device 22. The cane parameters 70, for example, may describe a length 72 of the walking cane 20, a material 74 associated with the walking cane 20, a shape 76 of the walking cane, and a cross-sectional shape 78 and/or area 80 of the walking cane 20. The cane parameters 70 may even include a current tip location 82 of the tip (illustrated as reference numeral 30 in FIG. 1) of the walking cane 20 (perhaps as determined by a GPS receiver in the walking cane 20). The tip location 82 of the tip of the walking cane 20 may help avoid obstacles, as later paragraphs will explain. The cane parameters 70, however, may describe any characteristics associated with the walking cane 20 that suit any purpose or designer.

Figure 5:
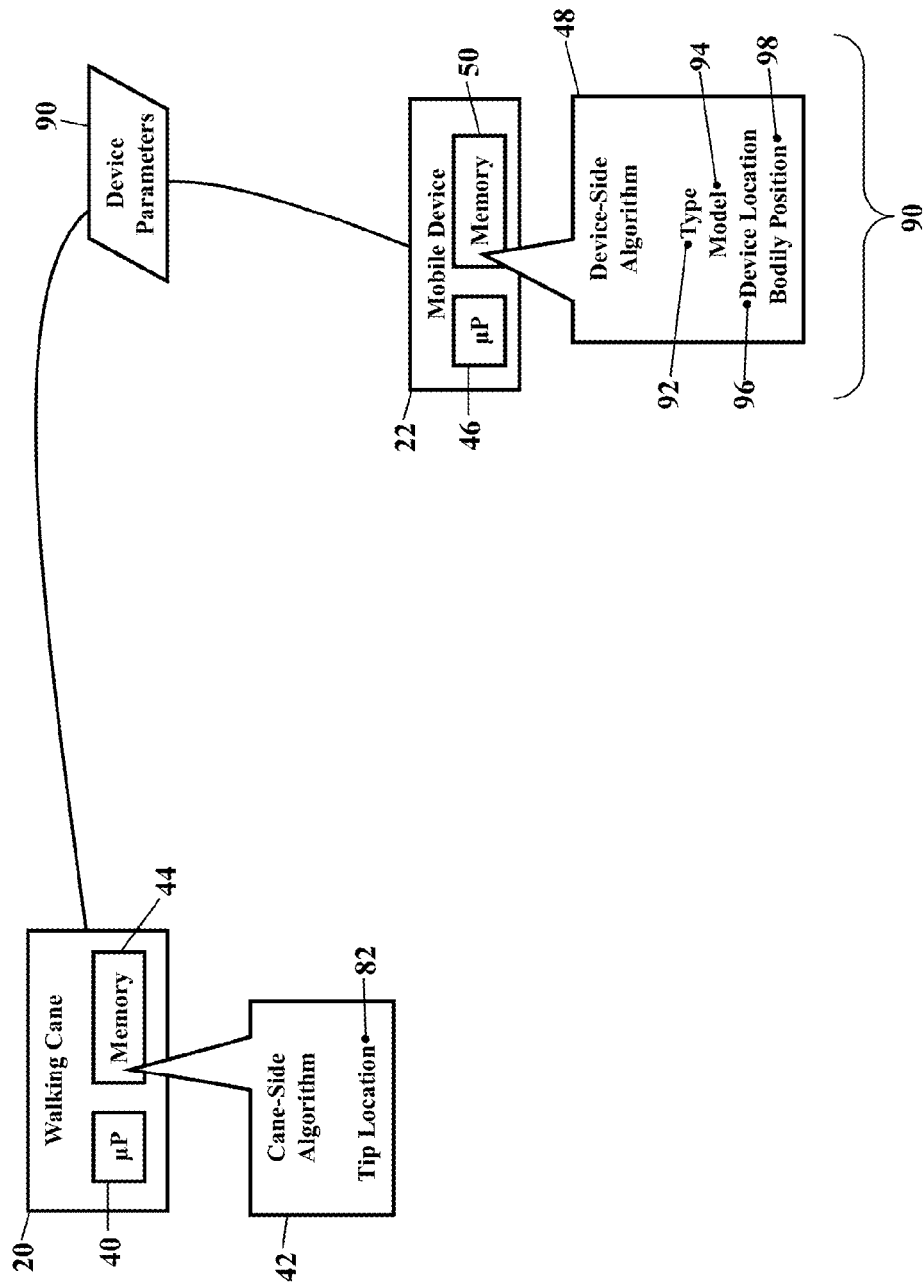

FIG. 5 illustrates device parameters 90. The device parameters 90 describe any characteristics associated with the mobile device 22. FIG. 5 illustrates the device parameters 90 being locally stored in the memory 50 of the mobile device 22. During the electronic pairing operation, the mobile device 22 may retrieve any of the device parameters 90 from the memory 50 and send the device parameters 90 to the walking cane 20. The device parameters 90, for example, may describe a type 92 of the mobile device 22, a model 94 of the mobile device 22, a device location 96 of the mobile device 22, and a bodily position 98 of the mobile device 22. Using a common example, the device parameters 90 may describe the mobile device 22 as an APPLE® IPHONE® 5 having a current device location 96 at some global positioning system ("GPS") coordinates. Moreover, the bodily position 98 may reflect the mobile device 22 being worn with a lanyard around a neck of the user or carried in the user's hand. The bodily position 98, in other words, may alter or modify the current tip location 82 to correctly and to safely avoid obstacles, as later paragraphs will explain.

Figure 6:
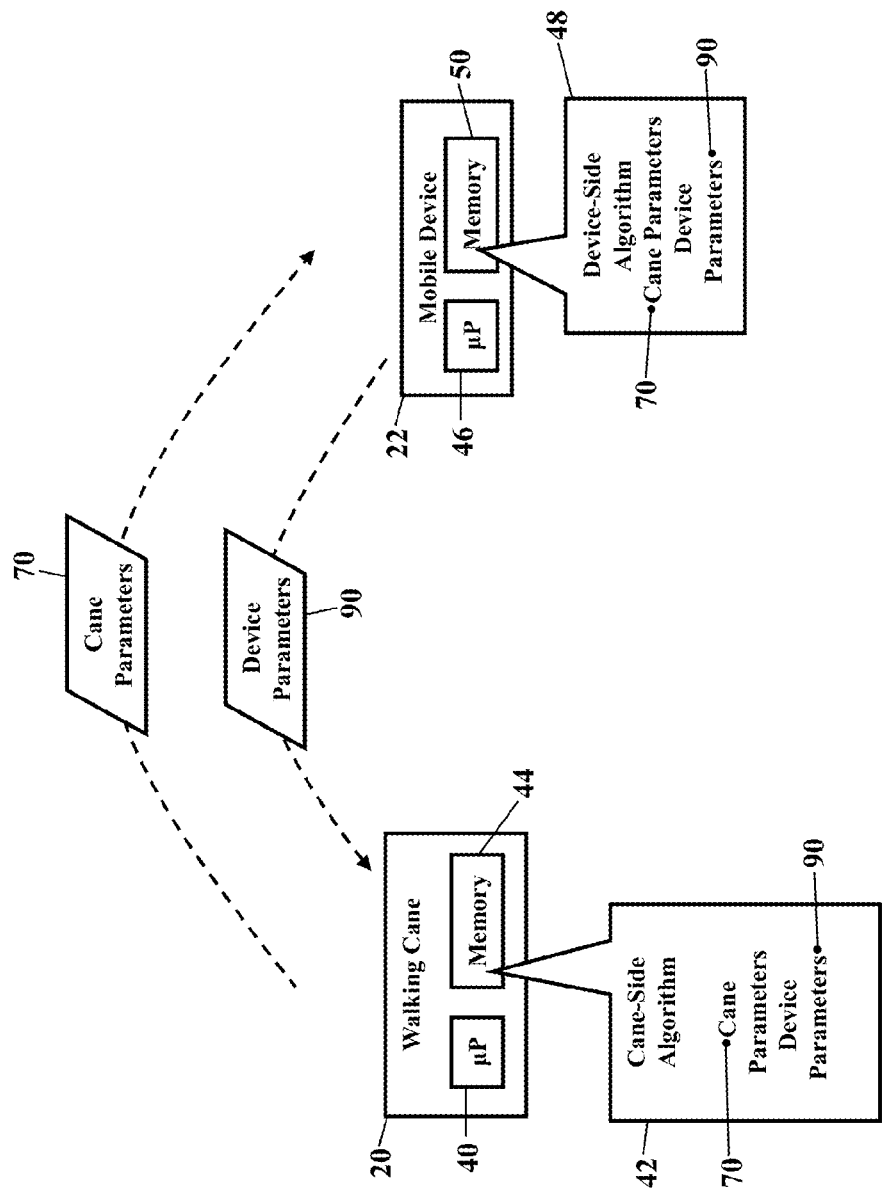

FIG. 6 further illustrates the electronic pairing. During the electronic pairing operation, the walking cane 20 may retrieve any of its cane parameters 70 and send the cane parameters 70 to the mobile device 22. The mobile device 22, likewise, may retrieve any of its device parameters 90 and send the device parameters 90 to the walking cane 20. Once the cane parameters 70 and/or the device parameters 90 are known, the cane-side algorithm 42 and the device-side algorithm 48 may cooperate to help avoid obstacles in the user's path.

Figure 7:
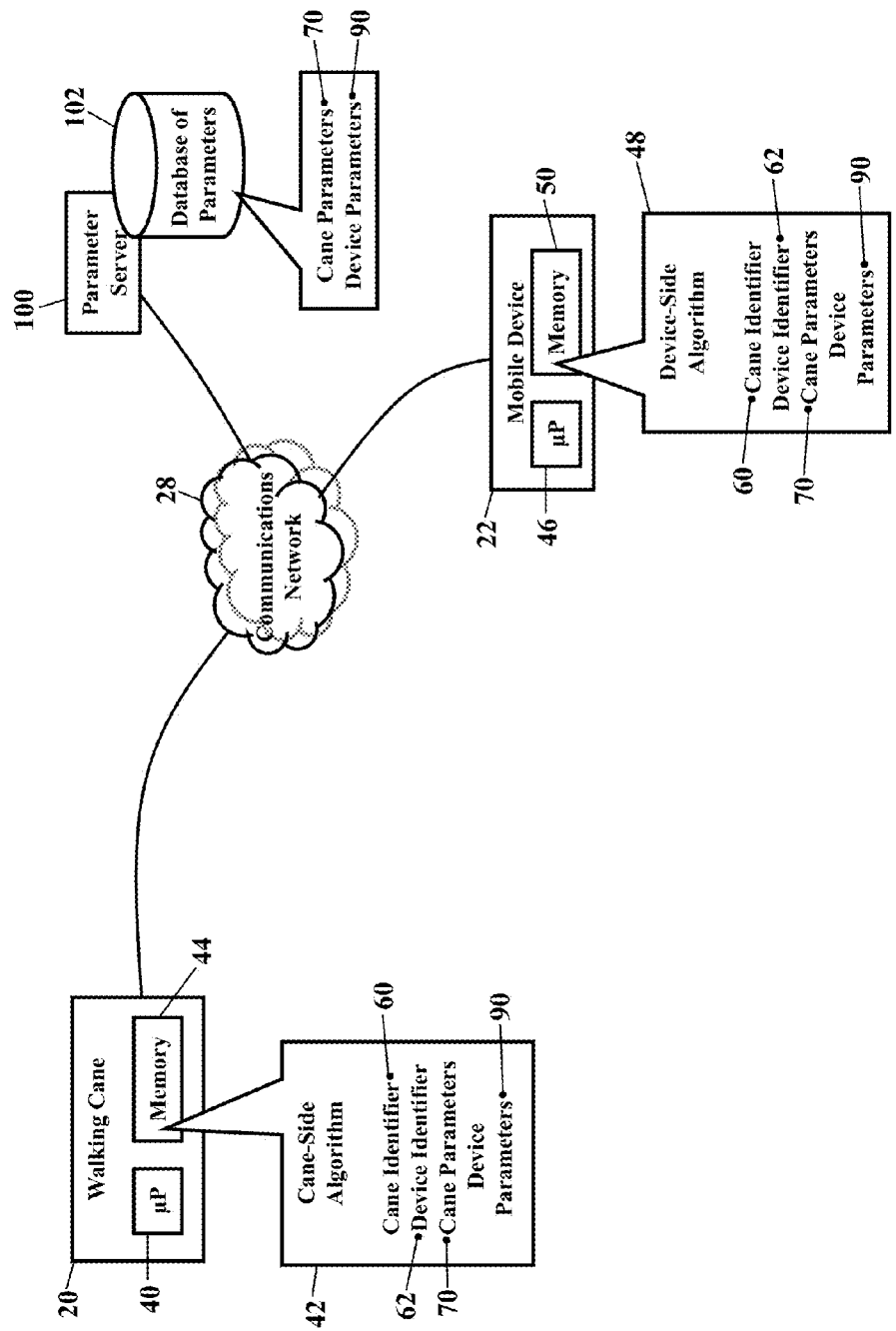
Figure 8:
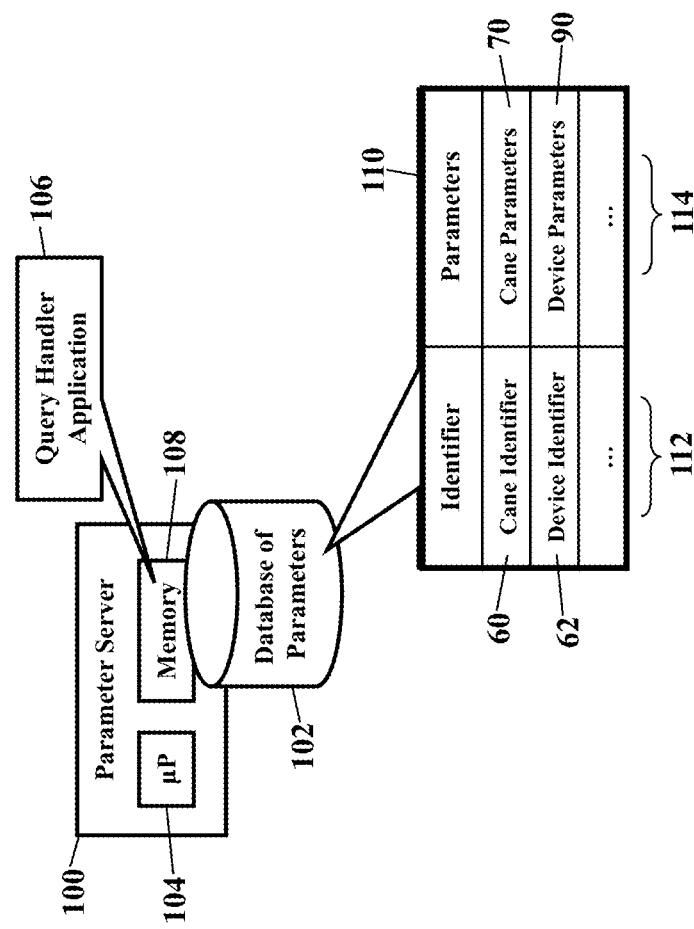

FIGS. 7-8 illustrate remote retrieval of pairing parameters. Here the cane parameters 70 and/or the device parameters 90 may be remotely retrieved from any location in the communications network 28. FIG. 7, for example, illustrates a parameter server 100 operating in the communications network 28. During the pairing operation, the walking cane 20 and/or the mobile device 22 may send queries to the parameter server 100. The queries may include the cane identifier 60 and/or the device identifier 62. When the parameter server 100 receives a query, the parameter server 100 queries a database 102 of parameters.

FIG. 8 further illustrates the parameter server 100. The parameter server 100 has a processor 104 that executes a query handler application 106 stored in memory 108. The database 102 of parameters is illustrated as a table 110 that maps, associates, or relates different identifiers 112 to their corresponding parameters 114. The parameter server 100, for example, retrieves the cane parameters 70 associated with the cane identifier 60. The parameter server 100 then responds to the query by sending the cane parameters 70 to a network address associated with the mobile device 22. If the query originated from the walking cane 20, then parameter server 100 sends the device parameters 90 to the network address associated with the walking cane 20. The database 102 of parameters may thus be a network-centric resource that is populated with many different identifiers 112 of different walking canes and any devices that interface with the walking canes. Each different identifier 112 is associated to its corresponding parameters 114. The database 102 of parameters may be a central repository that allows electronic pairing of walking canes and mobile devices connected to the communications network 28.

Once the walking cane 20 and the mobile device 22 electronically pair, the walking cane 20 and the mobile device 22 may cooperate for any reason. As the above paragraphs have mentioned, the walking cane 20 and the mobile device 22 may cooperate to avoid obstacles in the user's path. As the user carries the mobile device 22, the user may fail to see fire hydrants, curbs, stop signs, light posts, or any other obstacles in the user's path. While even normal-sighted users can fail to appreciate obstacles, the visually impaired may especially benefit from obstacle avoidance.

Figure 9:
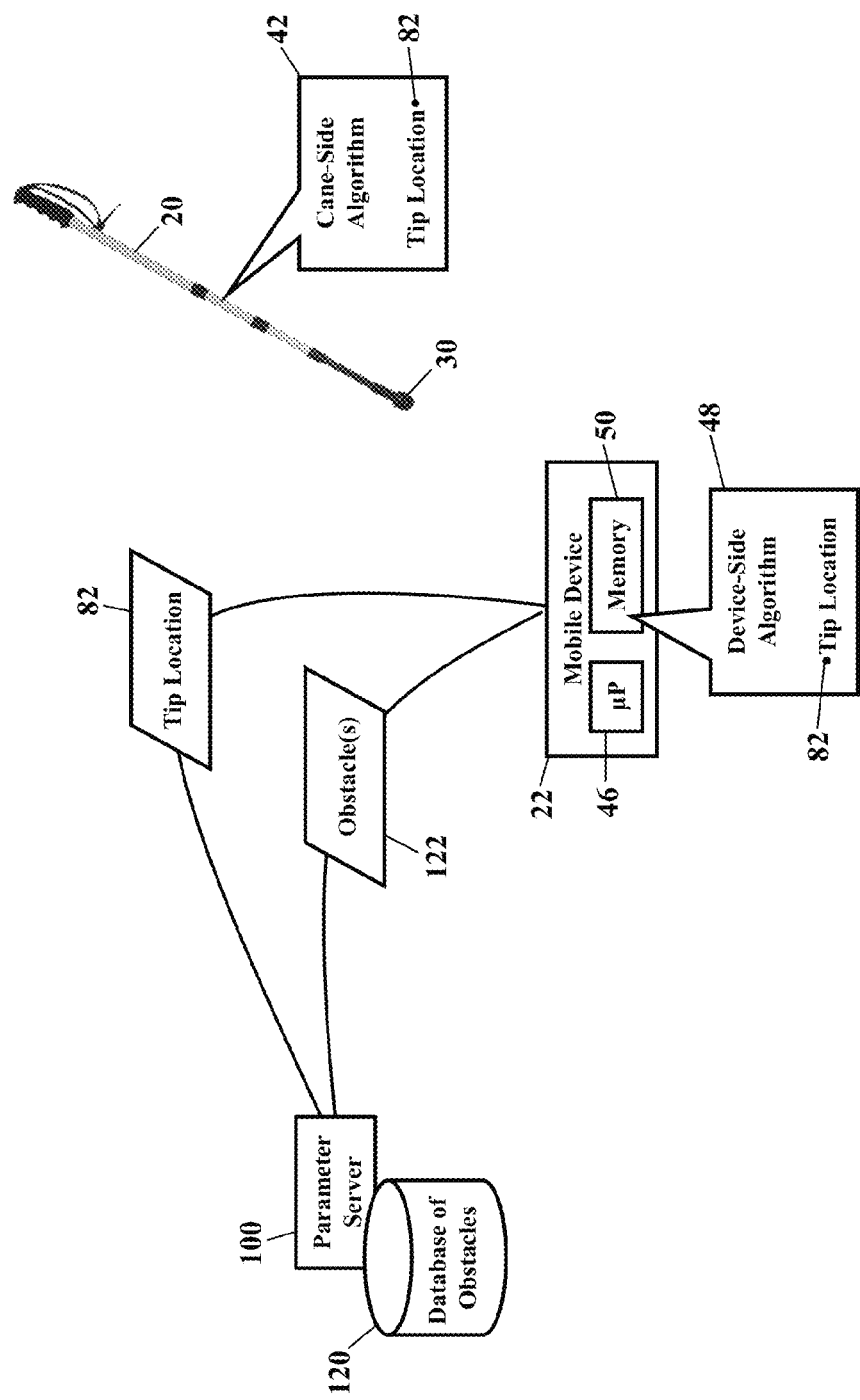
FIGS. 9-11 are schematics illustrating obstacle avoidance, according to exemplary embodiments.
Figure 10:
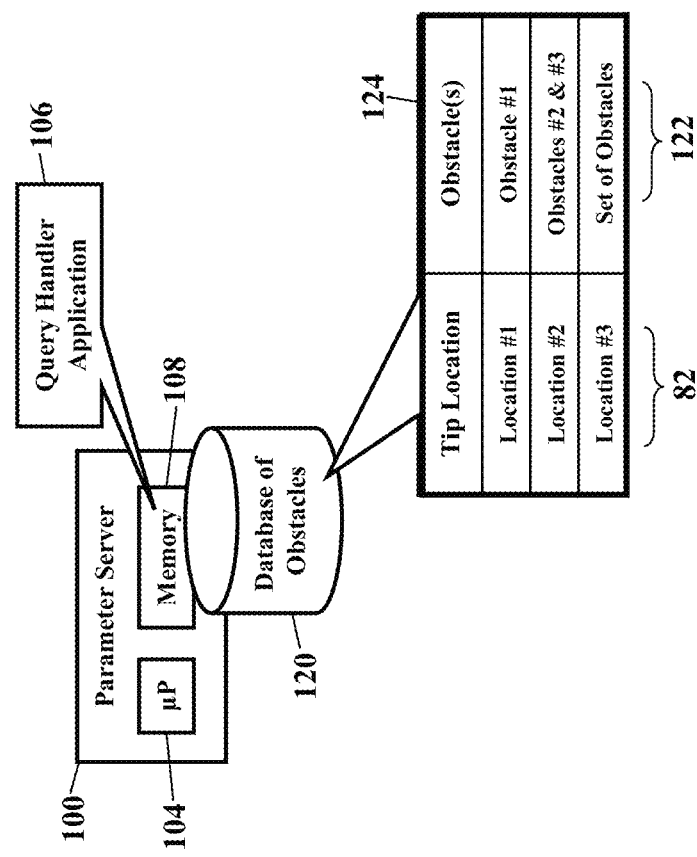
Figure 11:
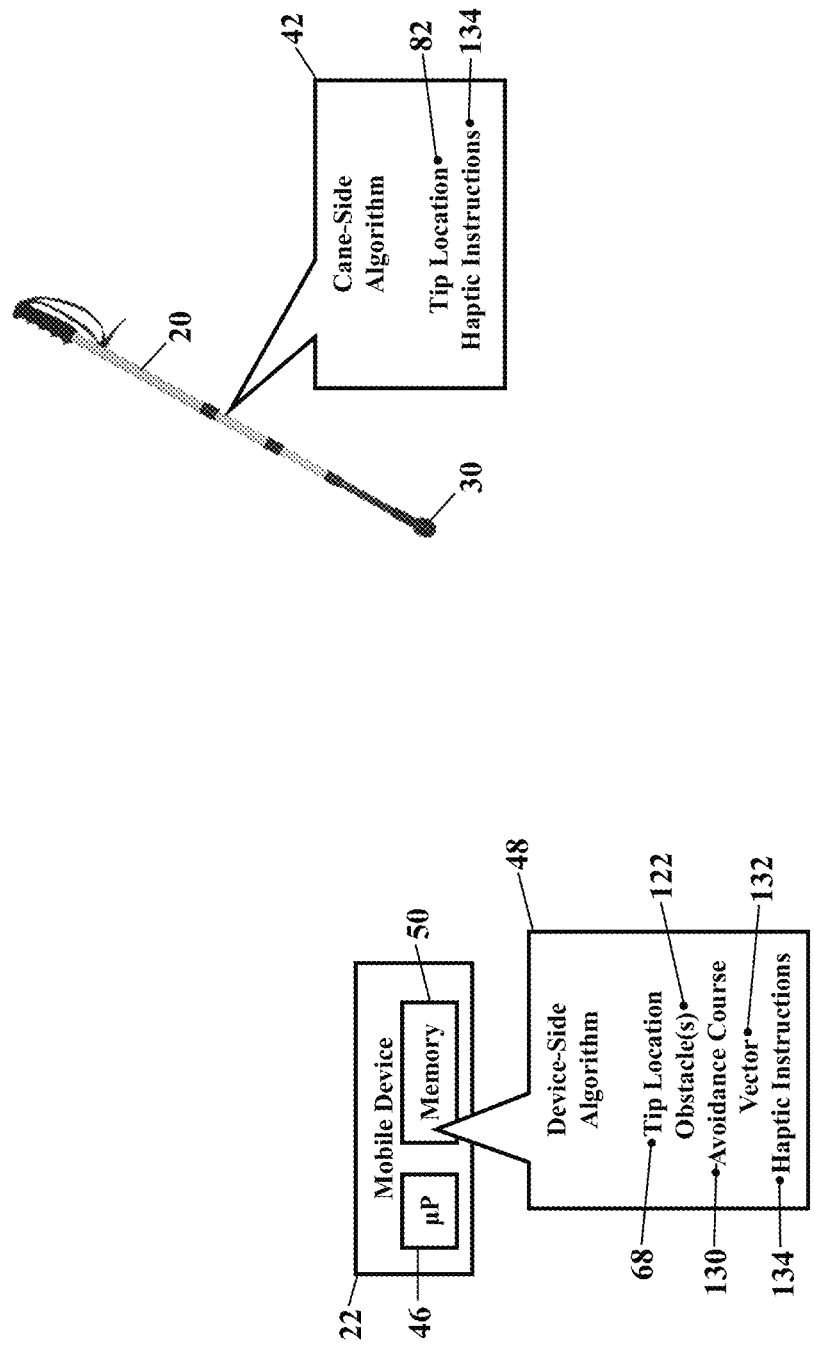

FIGS. 9-11 illustrate one such scheme for obstacle avoidance, according to exemplary embodiments. As the user carries the mobile device 22, location-based obstacle avoidance may be performed. The device-side algorithm 48 obtains the current tip location 82 (such as GPS coordinates) of the tip 30 of the walking cane 20. The device-side algorithm 48 may then query a database 120 of obstacles for the current tip location 82 of the tip 30 of the walking cane 20. For simplicity, the database 120 of obstacles is illustrated as being locally stored in the parameter server 100. The database 120 of obstacles, however, may be stored in any device or resource that is locally and/or remotely accessible to the mobile device 22. Regardless, the database 120 of obstacles stores locations of known obstacles. The database 120 of obstacles, for example, stores GPS coordinates for fire hydrants, utility poles, sewer grates, curbs, stop signs, and any other objects, areas, roads, buildings, or conditions considered hazardous. The database 120 of obstacles retrieves any obstacles 122 that are associated to the current tip location 82 of the tip 30 of the walking cane 20. The obstacles 122 are sent in a query response to the address associated with the mobile device 22.

FIG. 10 further illustrates the database 120 of obstacles. The database 120 of obstacles is queried for the current tip location 82. FIG. 10 illustrates the database 120 of obstacles as a table 124 that maps, associates, or relates different tip locations 68 to the corresponding obstacles 122. The query handler application 106 retrieves the obstacles 122 that match the current tip location 82 of the tip 30 of the walking cane 20. Each obstacle 122, for example, may be defined by its location, such as GPS coordinates. The device-side algorithm 48 thus retrieves the GPS coordinates of any known obstacles 122 that match the current tip location 82 of the tip 30 of the walking cane 20. The obstacles 122 are then sent in a query response to the Internet Protocol address of the mobile device 22.

FIG. 11 further illustrates obstacle avoidance. Once the obstacles 122 are known, the device-side algorithm 48 may then take actions to avoid those obstacles 122. The device-side algorithm 48, for example, may produce audible, visual, and/or haptic warnings of the obstacles 122. The device-side algorithm 48 may even plot an avoidance course 130 to avoid the obstacles 122. The device-side algorithm 48, for example, may cause the processor 46 to generate audible, visual, and/or haptic instructions to move the tip 30 of the walking cane 20 to avoid the obstacles. The device-side algorithm 48 may generate a tip vector 132 from the current tip location 82 of the tip 30 to some safe direction that avoids the obstacles 122. Exemplary embodiments may thus avoid the obstacles 122 in the path of the tip 30 of the walking cane 20, which is more relevant to visually impaired users than conventional obstacle avoidance schemes based on locations of the mobile device 22.

Haptic feedback may also be generated. Once the obstacles 122 are determined, the device-side algorithm 48 may also cause the processor 46 to generate haptic instructions 134. The haptic instructions 134 may be sent to the walking cane 20 for execution. The haptic instructions 134, for example, may instruct the cane-side algorithm 42 to provide haptic feedback to the user of the walking cane 20. The cane-side algorithm 42, for example, may cause the processor (illustrated as reference numeral 40 in FIGS. 2-7) in the walking cane 20 to activate a haptic generator in a handle or body of the walking cane 20. The haptic feedback thus alerts the user that the obstacle 122 may be encountered. Any audible or visual warnings may provide instructions for the user to move the walking cane 20 in a different direction (such as the tip vector 132). The haptic instructions 134 may even cause the walking cane 20 to generate haptic feedback in the direction of the tip vector 132. That is, the walking cane 20 may even have an electromechanical mechanism that turns, swivels, or orients the walking cane 20 to the tip vector 132. The tip vector 132 and/or the haptic instructions 134 may be expressed as yaw, pitch, and roll commands which processor 40 in the walking cane 20 executes.

Figure 12:
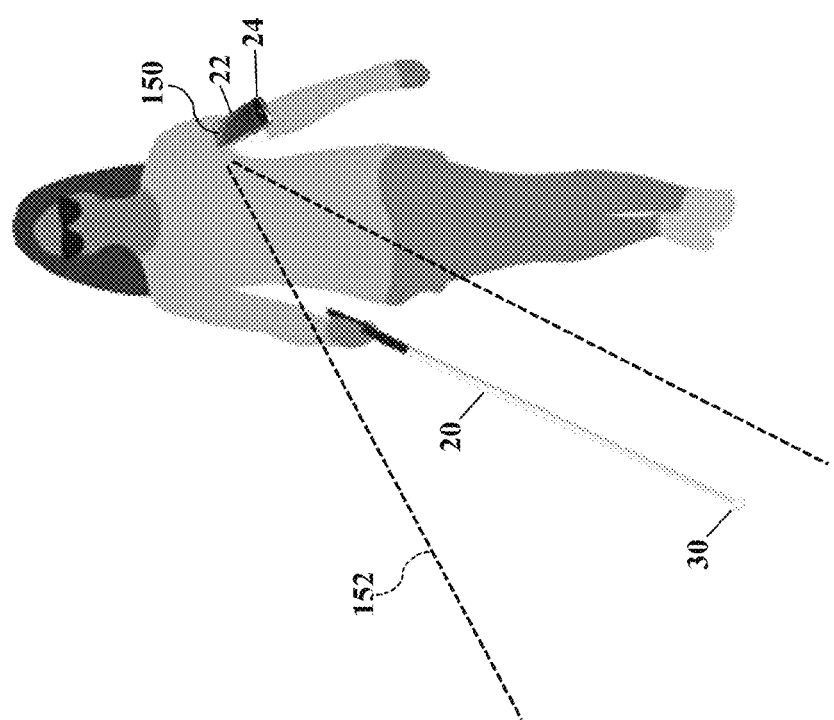
FIGS. 12-17 are schematics illustrating another scheme for obstacle avoidance, according to exemplary embodiments.

FIGS. 12-17 illustrate another scheme for obstacle avoidance, according to exemplary embodiments. Here, exemplary embodiments may use triangulation and/or image analysis to infer a distance between the tip 30 of the walking cane 20 and the mobile device 22. As the user carries the mobile device 22, a digital camera 150 may be instructed to capture one or more images 152 of the walking cane 20. FIG. 12 illustrates the digital camera 150 operating within the smart phone 24, but the digital camera 150 may be separate from the mobile device 22. Exemplary embodiments may then use the image 152 to infer the distance between the tip 30 of the walking cane 20 and the mobile device 22.

Figure 13:
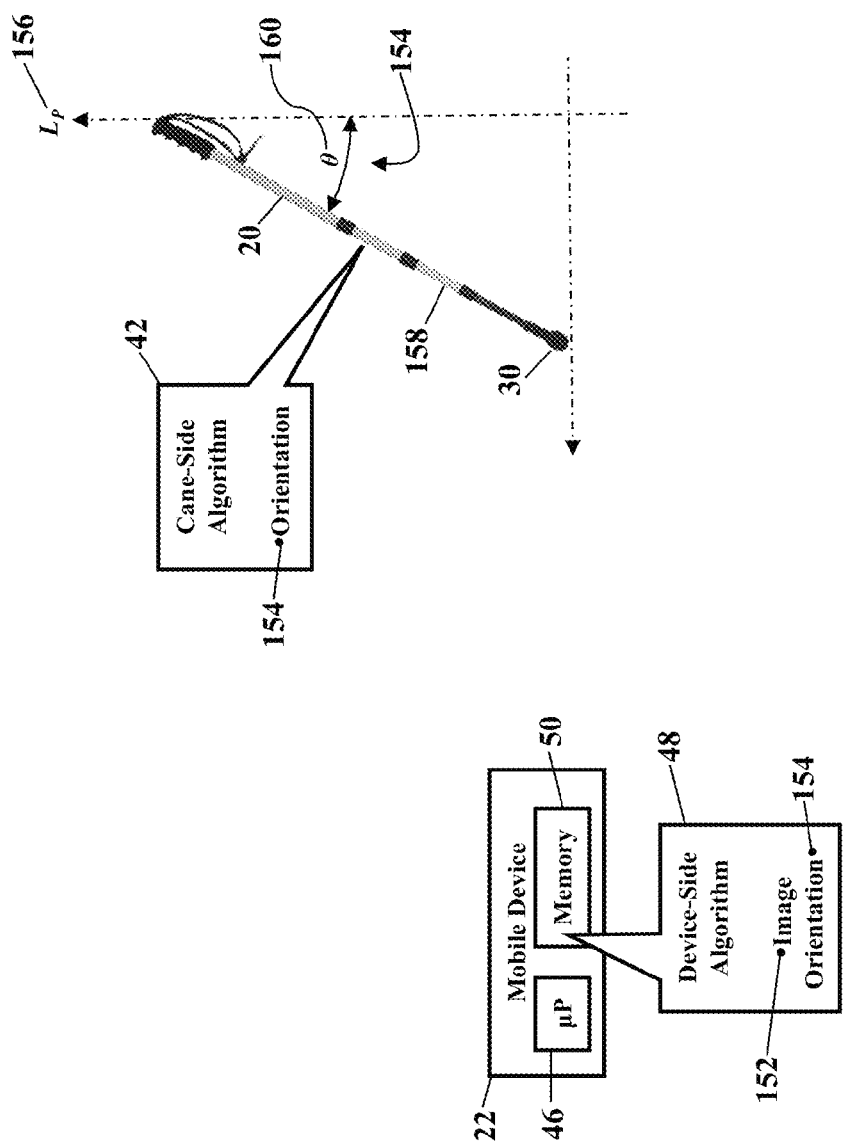

FIG. 13 illustrates an angular orientation 154 of the walking cane 20. As the user holds and walks with the walking cane 20, the walking cane 20 has some angular orientation 154. FIG. 13 illustrates the angular orientation 154 with respect to perpendicular $L_P$ (illustrated as reference numeral 156). The walking cane 20, for example, may include a sensor 158 that senses or determines an angle θ (illustrated as reference numeral 160) from perpendicular $L_P$. The sensor 158 may be an inclinometer, tilt sensor, accelerometer, mercury switch, or any other means of measuring the orientation 154 of the walking cane 20. The walking cane 20 may then transmit or send the orientation 154 to the mobile device 22.

Figure 14:
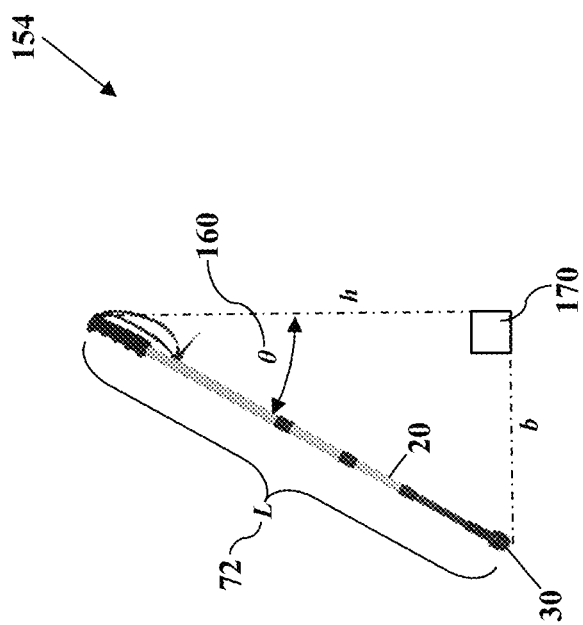
Figure 15:
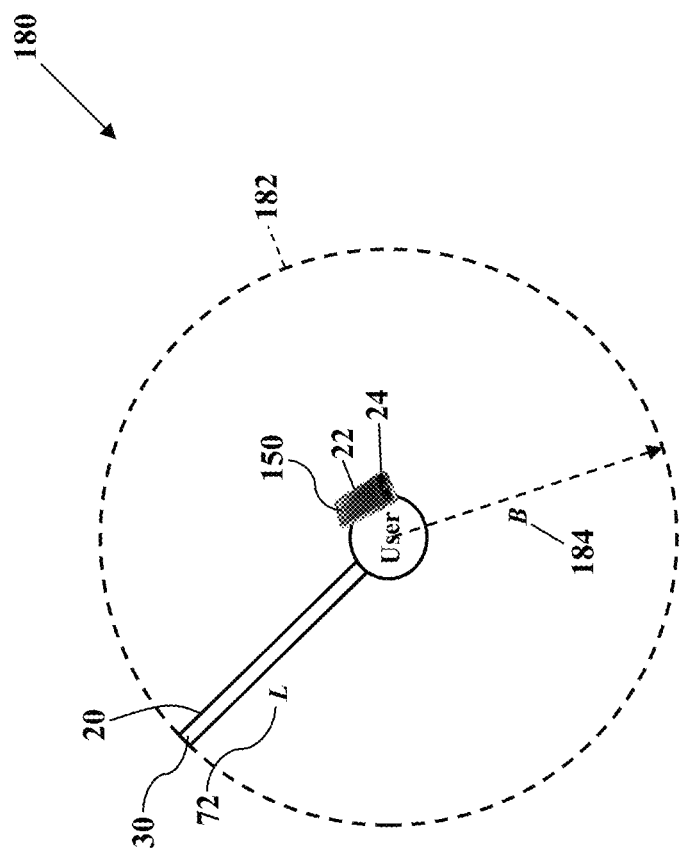

FIGS. 14-15 thus illustrate trigonometric relationships based on the length 72 of the walking cane 20. As the user holds and walks with the walking cane 20, FIG. 14 illustrates a right triangle 170 that may be assumed from the orientation

154 of the walking cane 20. The length 72 of the walking cane 20 may be denoted as the hypotenuse, L, of the right triangle 170. The base, b, of the right triangle 170 may be calculated from $$b = L \sin \theta,$$

and the height, h, of the right triangle 170 may be calculated from $$h = L \cos \theta.$$

The lengths of all sides (L, b, and h) of the right triangle 170 may thus be defined from trigonometric relationships.

FIG. 15 illustrates a zone 180 about the mobile device 22. The zone 180 is illustrated as a circle 182, but the zone 180 may have any shape. The zone 180 may also be mathematically defined based on trigonometric relationships and the length 72 of the walking cane 20. As the user holds and walks with the walking cane 20, the zone 180 may be mathematically defined around the user, based on the length 72 of the walking cane 20. If the digital camera 150 is assumed to lie within the zone 180, the circle 182 has an area with radius B (illustrated as reference numeral 184). Comparing FIGS. 14 and 15, the radius B of the circle 182 will thus vary according to the orientation 154 of the walking cane 20. Using trigonometric relationships, the radius B of the circle 182 varies as $B(\theta)$ and may be calculated from $$B(\theta) = L \sin \theta.$$

The maximum distance from the digital camera 150 (in the mobile device 22) to the tip 30 of the walking cane 20 occurs when the walking cane 20 is held horizontal. If the maximum distance is denoted as $D(\theta, x)$, the maximum distance is $$D_{Max} = 2 \times B(\theta) = 2 \times L \text{ when } \theta \text{ is zero degrees.}$$

The maximum distance $D_{Max}$, in other words, is twice the length 72 of the walking cane 20 when held horizontal.

Figure 16:
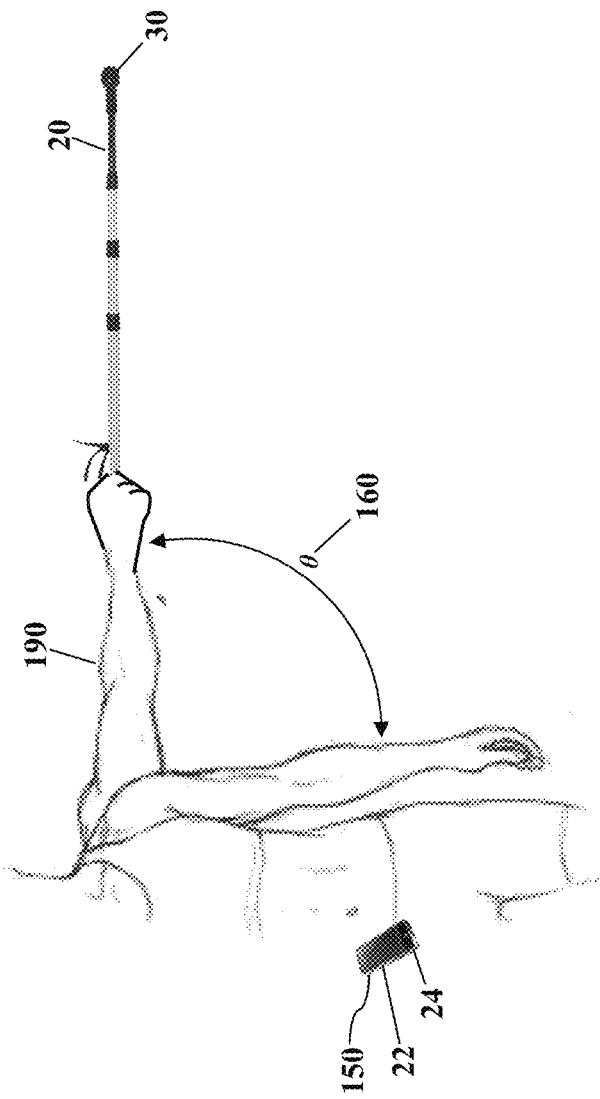
Figure 17:
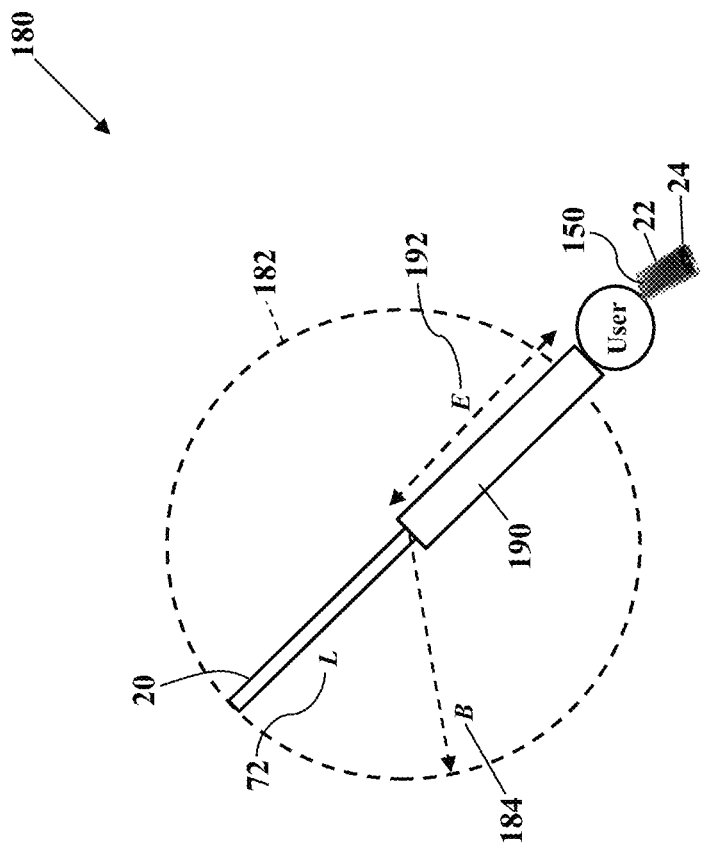

FIGS. 16-17 illustrate an alternate scenario for the zone 180. FIG. 16 illustrates the user's arm 190 holding the walking cane 20. The user's arm 190 is outstretched, with the walking cane 20 horizontally held. That is, the angle θ (illustrated as reference numeral 160) of the walking cane 20 is ninety degrees (90°) from vertical (or zero degrees from horizontal). Because the user's arm 190 is outstretched, FIG. 17 illustrates how the digital camera 150 may lie outside the circle 182, due to the user's outstretched arm 190. Because the circle 182 is offset by the user's outstretched arm 190, the maximum distance $D_{Max}$ may thus be based on the length 72 of the walking cane 20 and an arm length E of the user's arm 190. The arm length E (illustrated as reference numeral 192) may be stored in memory of walking cane 20 and/or the mobile device 22 and sent during the electronic pairing. Here, then, maximum distance $D_{Max}$ is $$D_{max} = E + B(\theta),$$

which simplifies to $D_{Max} = E + L$ when θ is zero degrees. Again, then, the maximum distance $D_{Max}$ occurs when the user extends her arm 190 and horizontally holds the walking cane 20.

Figure 18:
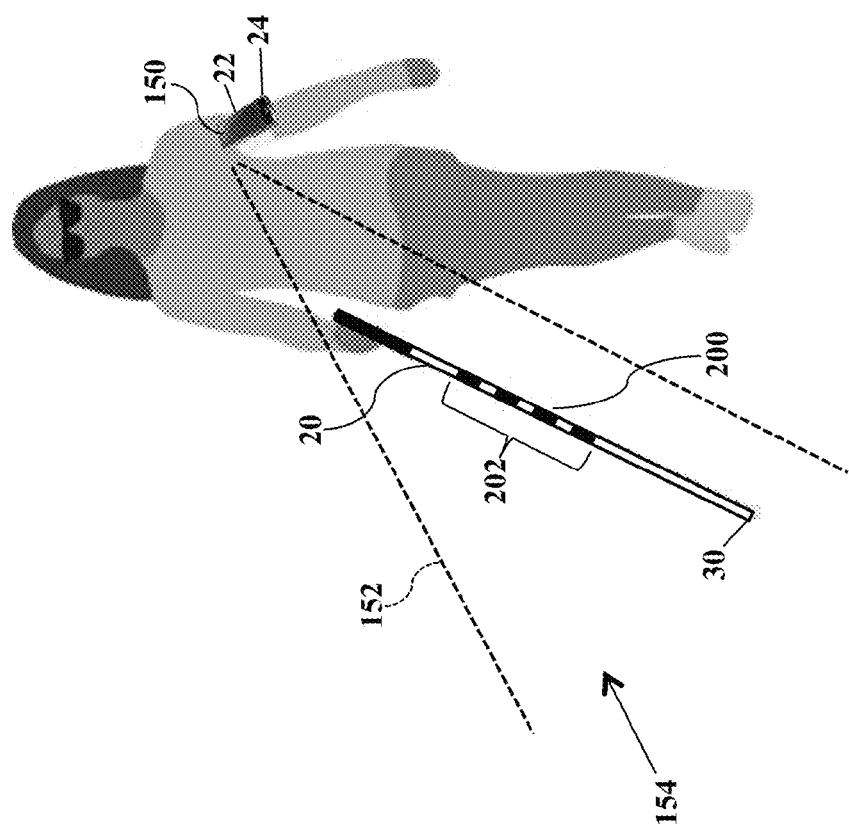
FIGS. 18-20 are schematics illustrating cane markings, according to exemplary embodiments.
Figure 19:
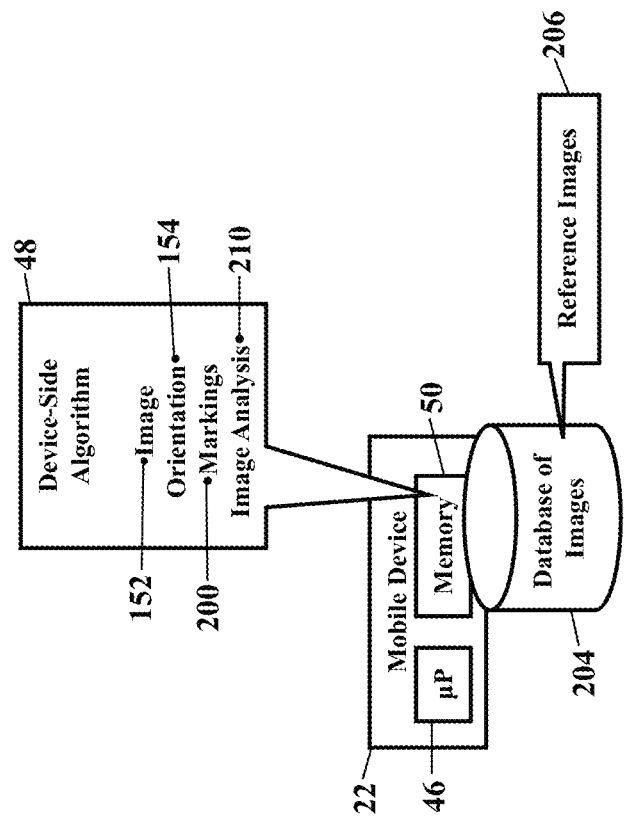
Figure 20:
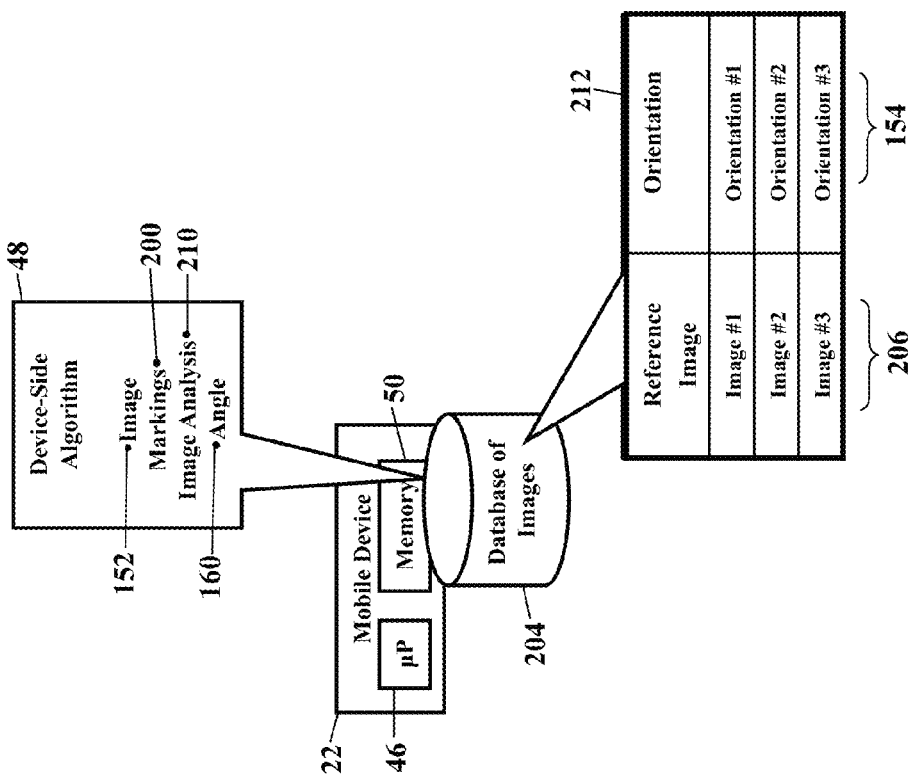

FIGS. 18-20 are schematics illustrating cane markings 200, according to exemplary embodiments. The markings 200 are applied or adorned to the walking cane 20. The device-side algorithm 48 uses the markings 200 to further refine the orientation 154 of the walking cane 20. As the user carries the mobile device 22, the digital camera 150 captures the one or more images 152 of the walking cane 20. The markings 200 may be any means for recognizing the orientation 154 of the walking cane 20 in the current image 150. The walking cane 20, for example, may have a polygonal cross section (such as a pentagonal, hexagonal, or octagonal cross-section) with faceted or flat longitudinal surfaces. The markings 200, however, may also be any image, sticker, logo, pattern, wording, paint, color, barcode, or symbol that is observable in the image 150. FIG. 18, for simplicity, illustrates the markings as contrasting black and white stripes 202 applied to a longitudinal shaft or body of the walking cane 20. As FIG. 19 illustrates, the device-side algorithm 48 then compares the image 152 to a database 204 of images. The database 204 of images stores one or more reference images 206 of the walking cane 20. The device-side algorithm 48 uses image analysis 210 to compare the markings 200 in the recent image 152 to the reference images 206 of the walking cane 20. The markings 200 are thus visual cues for calculating the orientation 154 of the walking cane 20.

FIG. 20 further illustrates the database 204 of images. The reference images 206 are digital images of the markings 200 on the walking cane 20. The database 204 of images associates each reference image 206 to the corresponding orientation 154 of the walking cane 20. By comparing the markings 200 in the recent image 152 to the markings 200 in the reference images 206, exemplary embodiments may further refine or determine the current orientation 154 of the walking cane 20. FIG. 20 illustrates the database 204 of images as a table 212 that maps or relates each different reference image 206 to its associated orientation 154. When the current image 152 of the markings 200 matches one of the reference images 206, the device-side algorithm 48 retrieves the corresponding orientation 154. The device-side algorithm 48 may thus use the image analysis 210 to query the database 204 of images for the markings 200 in the current image 152 of the walking cane 20. Once the orientation 154 is known, the device-side algorithm 48 now knows the angle θ (illustrated as reference numeral 160). Exemplary embodiments may now use the trigonometric relationships to calculate the distance between the tip 30 of the walking cane 20 and the mobile device 22 (as earlier paragraphs explained).

Figure 21:
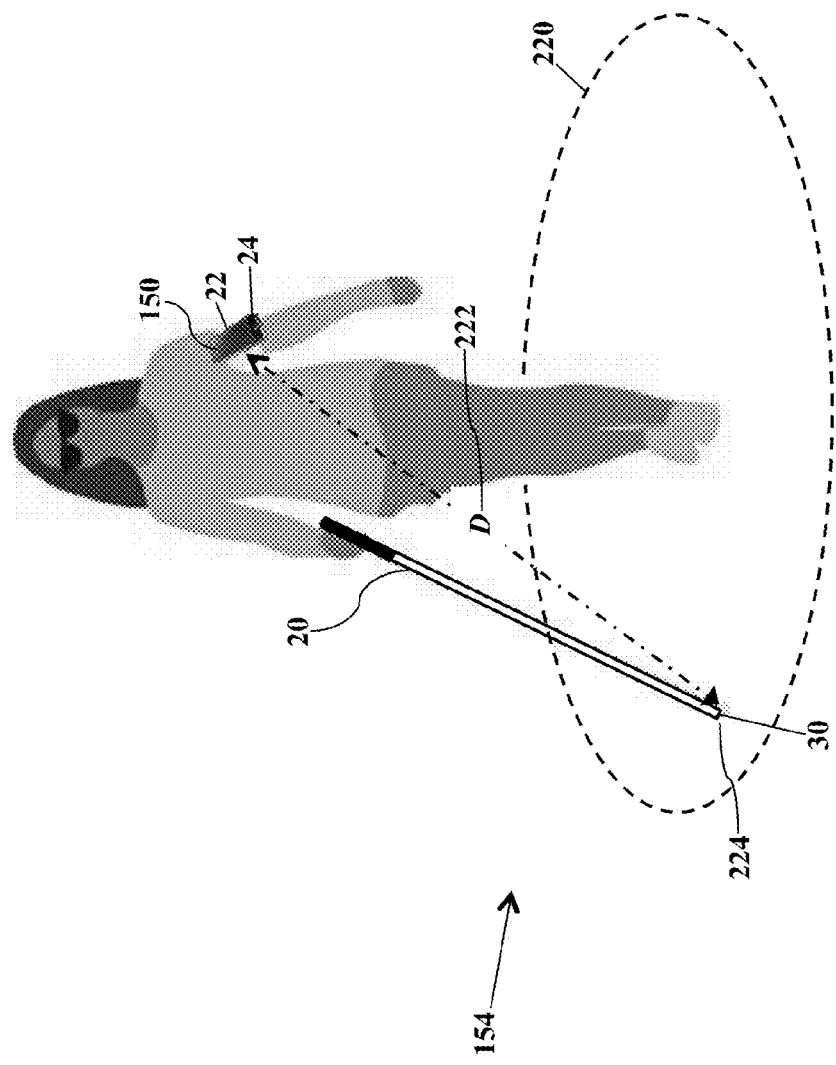
FIGS. 21-22 are schematics illustrating a wave diagram, according to exemplary embodiments.
Figure 22:
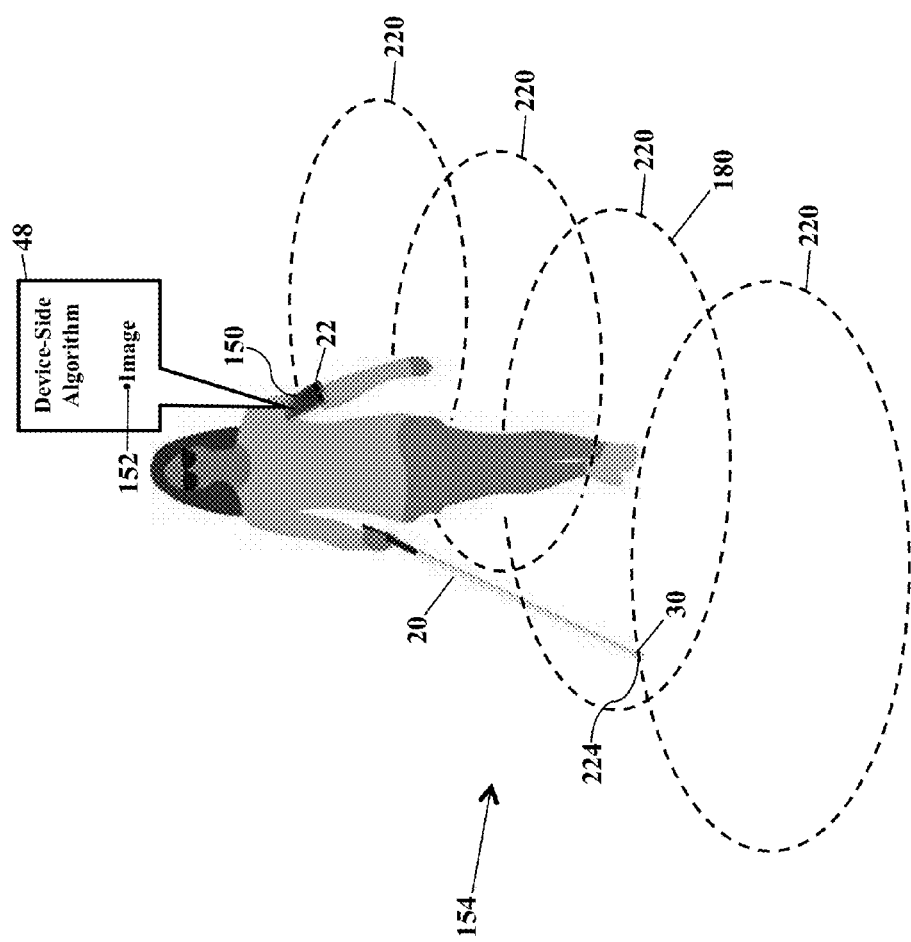

FIGS. 21-22 are schematics illustrating a wave diagram 220, according to exemplary embodiments. Once the orientation 154 of the walking cane 20 is known, exemplary embodiments may infer or calculate the distance D (illustrated as reference numeral 222) between the camera 150 and a point 224 of contact for the tip 30 of the walking cane 20. FIG. 21 thus illustrates the single wave diagram 220 having the diameter D, as determined from the orientation 154, as explained above.

FIG. 22 illustrates successive wave diagrams 220. As the user walks with the walking cane 20, exemplary embodiments may repeatedly calculate the wave diagram 220 for each impact of the tip 30 of the walking cane 20. The device-side algorithm 48 may instruct the camera 150 to repeatedly capture the image 152 and mathematically generate the wave diagram 220 with each step or at each point 224 of contact between the tip 30 and ground. FIG. 22 thus illustrates the successive wave diagrams 220 that are generated over time and distance.

Each wave diagram 220 may help avoid obstacles. As the user walks with the walking cane 20, the successive wave diagrams 220 may be used to avoid the obstructions that lie in the user's path. Each wave diagram 220 may thus represent the boundary zone 180 within which the user may be harmed by fire hydrants, curbs, and other obstacles in the walking path. The device-side algorithm 48 may thus query the database of obstacles (illustrated as reference numeral 120 in FIGS. 9-10) for known obstacles within the boundary zone 180 defined by each wave diagram 220. The device-side algorithm 48 may thus quickly calculate how far away the obstacle is from any point of reference with the wave diagrams 220. As the orientation 154 of the walking cane 20 changes with each step and/or with time, the wave diagrams 220 may change in size and perspective as a viewing angle of the camera 150 changes and as the location changes.

Figure 23:
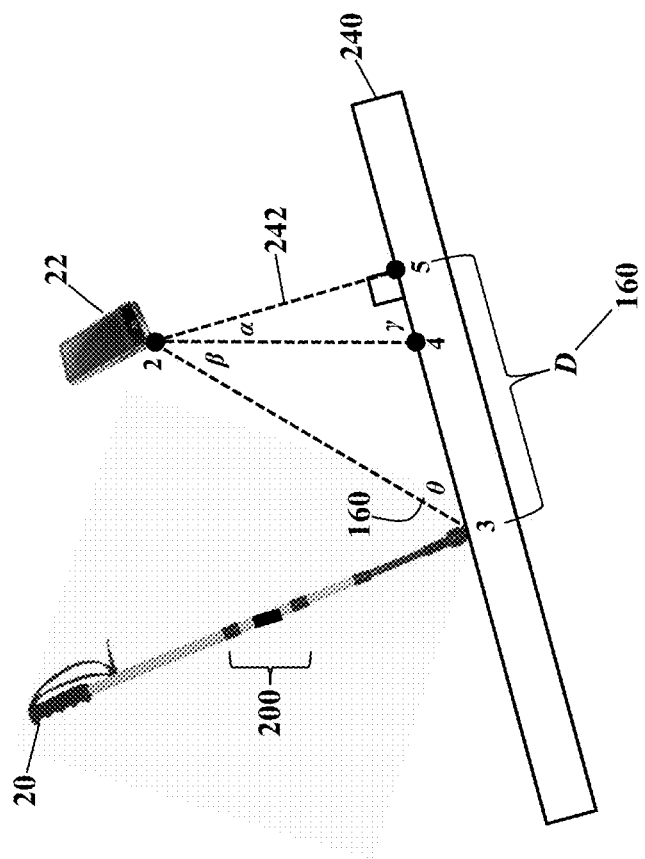
FIG. 23 is a free body diagram illustrating an orientation of a walking cane, according to exemplary embodiments.

FIG. 23 is a free body diagram illustrating the orientation 154 of the walking cane 20, according to exemplary embodiments. The orientation 154 of the walking cane 20 to the mobile device 22 may again be calculated using trigonometric relationships. Earth ground (illustrated as reference numeral 240) is assumed to a sloping plane. The height 242 of the camera 150 is predetermined from a set up angle ($\alpha$), which may be measured by an internal mechanism in the mobile device 22. The APPLE® IPHONE®, for example, may have a capability to measure the set up angle ($\alpha$) relative to perpendicular and a fixed back wall of the camera 150. The triangle having corners (2, 4, 5) is a right triangle having angles ($\alpha+\gamma$)=90°, with height H1 (2,4) equal to the height 242 of the camera 150 divided by $\cos(\alpha)$. The triangle having corners (2, 3, 5) is another right triangle having angles ($\theta+\beta+\alpha$)=90°, with height H2 (2,3) equal to the height 242 of the camera 150 divided by $\cos(\alpha+\beta)$. The angle $\theta$ (illustrated as reference numeral 160) is the orientation 154 based on the markings 200 on the walking cane 20, as explained above. The distance D (illustrated as reference numeral 160) from the camera 150 to the tip 30 of the walking cane 20 is $d(3,5)-H2\sin(\alpha+\beta)$.

Exemplary embodiments may resize the wave diagram 220 (illustrated in FIGS. 21-22). That is, the diameter D of the wave diagram 220 may be enlarged to provide an extra measure of safety around obstacles. Conversely, the diameter D of the wave diagram 220 may be reduced in confined or clutter spaces. Exemplary embodiments, for example, may retrieve a location-based scaling factor. When the GPS coordinates indicate a cluttered environment, the scaling factor may have a value less than 1.0, thus causing a reduction in the diameter D of the wave diagram 220. A relatively obstacle-free environment may have a greater than 1.0 scaling factor to enlarge the diameter D of the wave diagram 220.

Figure 24:
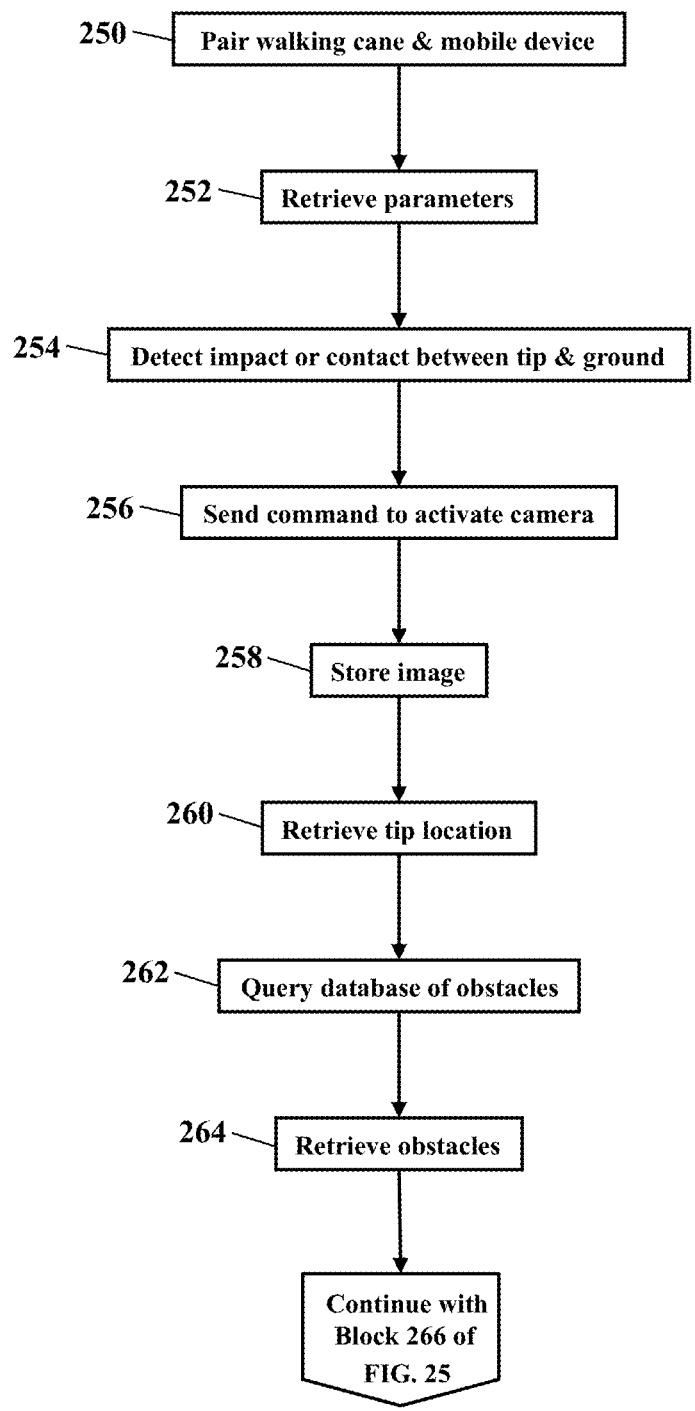
FIGS. 24-26 are flowcharts illustrating a method or algorithm for avoiding obstacles, according to exemplary embodiments.
Figure 25:
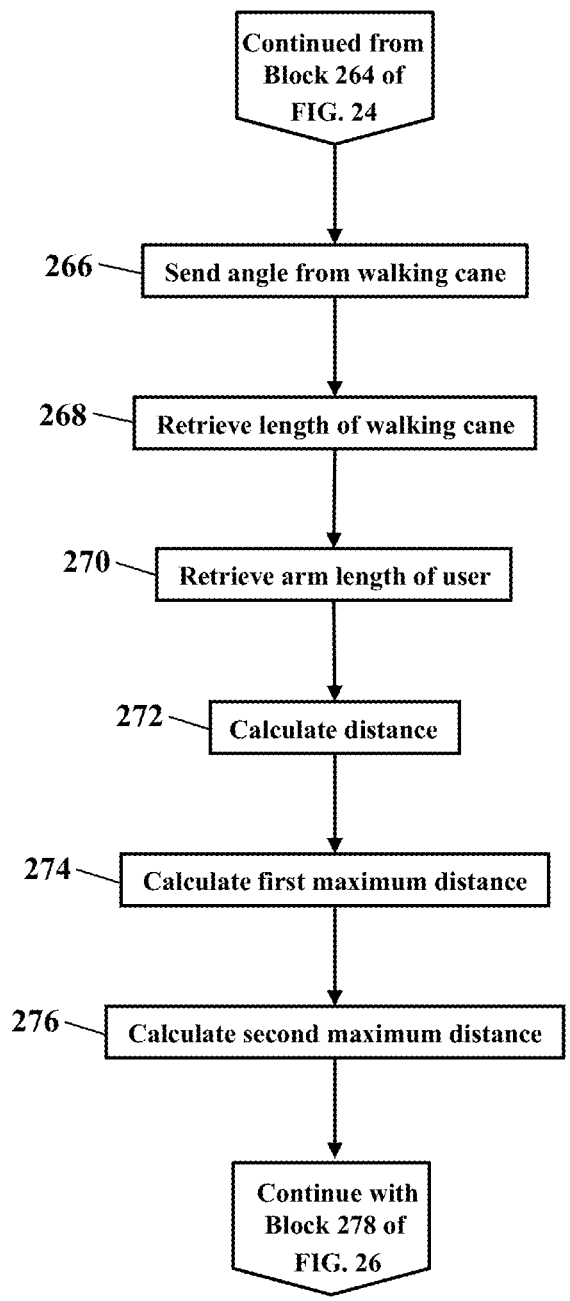
Figure 26:
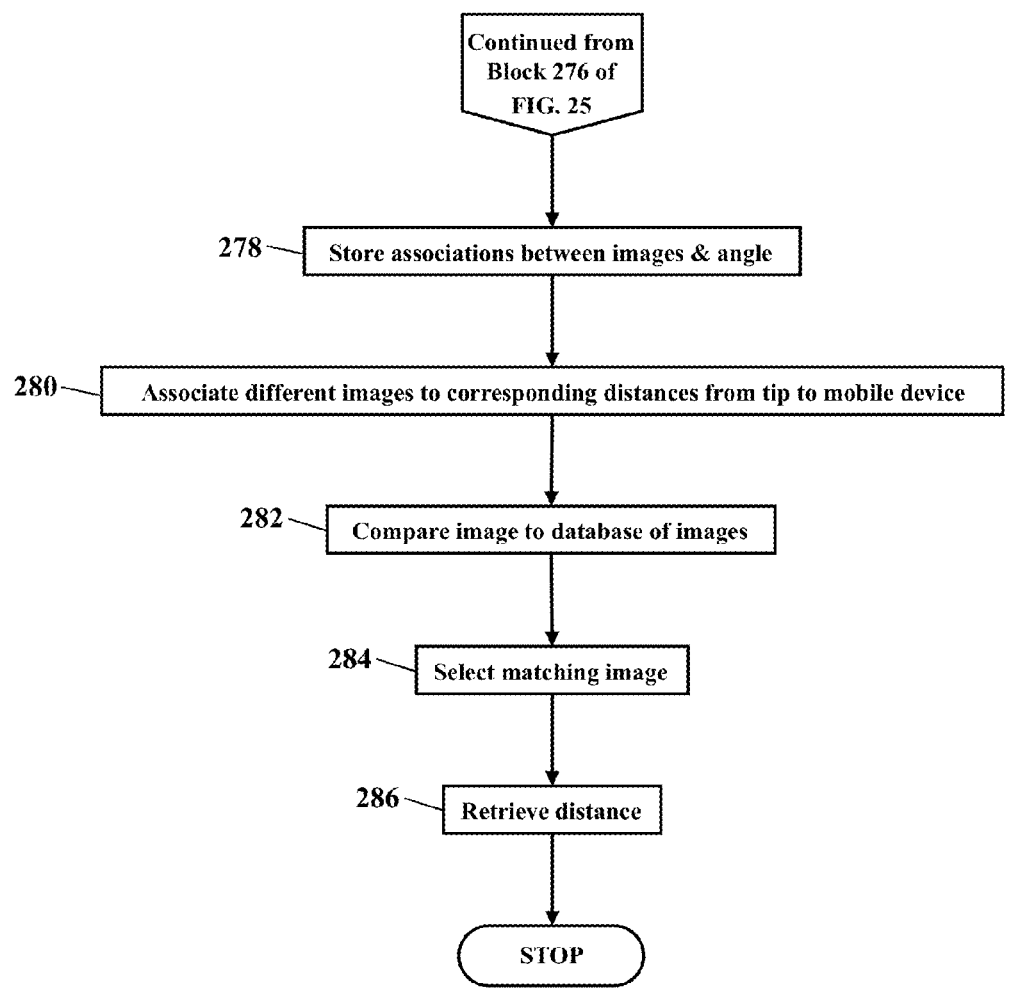

FIGS. 24-26 are flowcharts illustrating a method or algorithm for avoiding obstacles, according to exemplary embodiments. The walking cane 20 and the mobile device 22 electronically pair (Block 250). The parameters 64 are retrieved (Block 252). An impact sensor detects an impact or contact between the tip 30 of the walking cane 20 and Earth ground (Block 254). A command is sent from the walking cane 20 to the mobile device 22 to activate the camera 150 (Block 256). The image 152 of the walking cane 20 is stored (Block 258). The tip location 82 is retrieved (Block 260) and the database 120 of obstacles is queried (Block 262). The obstacles 122 are retrieved (Block 264).

The algorithm continues with FIG. 25. The walking cane 20 sends the orientation angle 160 to the mobile device 22 (Block 266). The length 72 of the walking cane 20 is retrieved (Block 268). The arm length 192 of a user's arm is retrieved (Block 270). The distance 222 from the tip 30 of the walking cane 22 to the mobile device 22 is calculated (Block 272). A first maximum for the distance 222 is calculated as twice the length 72 of the walking cane 20 (Block 274). A second maximum for the distance 222 is calculated as a sum of the length 72 of the walking cane 22 and the arm length 192 of the user (Block 276).

The algorithm continues with FIG. 26. Associations are stored between the image 152 of the walking cane 20 and the orientation angle 160 (Block 278). The database 204 of images associates different images of the walking cane 20 to corresponding distances 222 from the tip 30 of the walking cane 20 to the mobile device 22 (Block 280). The image 152 of the walking cane 20 is compared to the database 204 of images (Block 282). A matching image in the database 204 of images is selected (Block 284). The distance 222 is retrieved that is associated with the matching image in the database 204 of images (Block 286).

Figure 27:
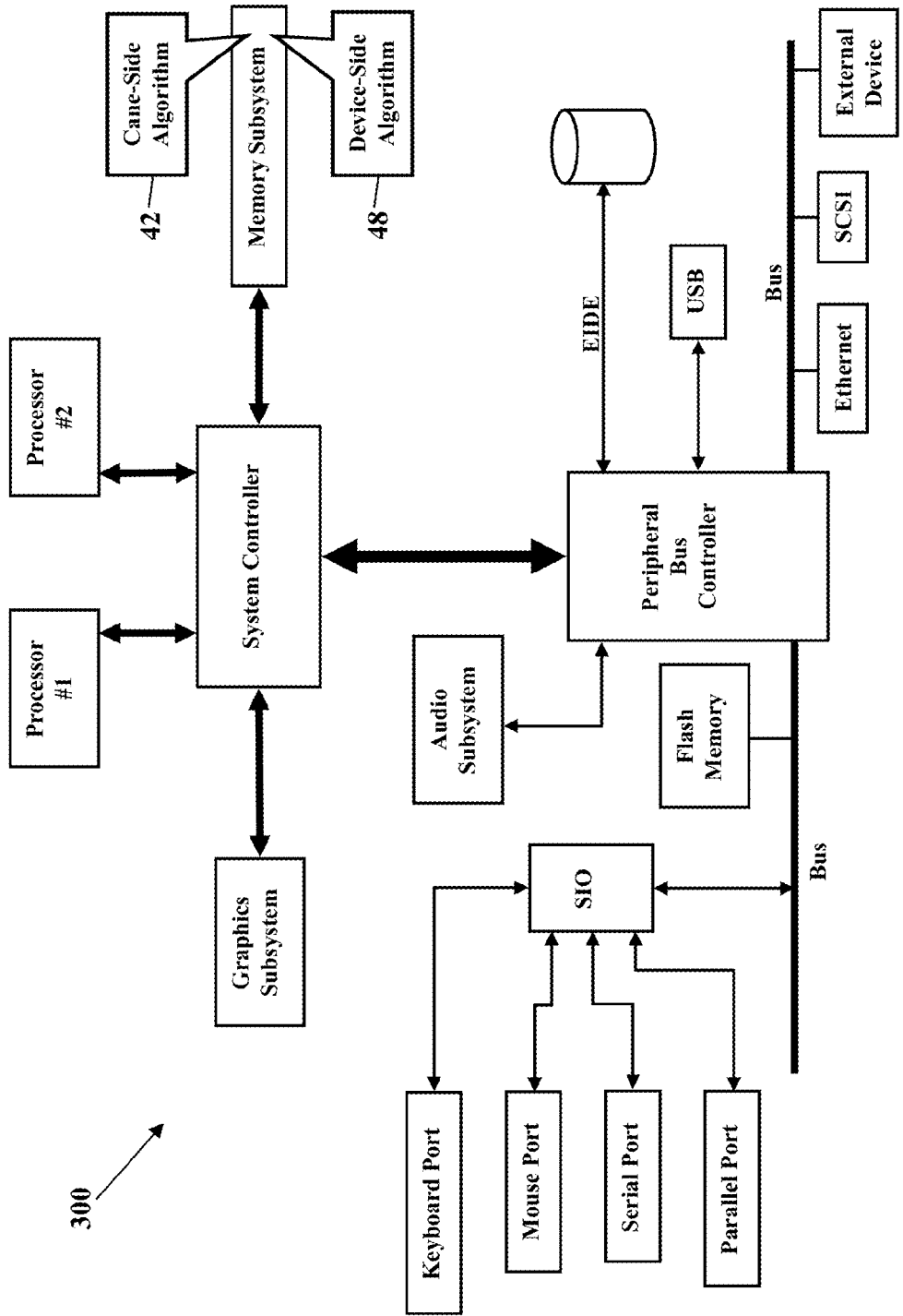
FIGS. 27-28 depict still more operating environments for additional aspects of the exemplary embodiments.

FIG. 27 is a schematic illustrating still more exemplary embodiments. FIG. 27 is a generic block diagram illustrating the cane-side algorithm 42 and the device-side algorithm 48 operating within a processor-controlled device 300. As the above paragraphs explained, the cane-side algorithm 42 and the device-side algorithm 48 may operate in any processor-controlled device 300. FIG. 27, then, illustrates the cane-side algorithm 42 and/or the device-side algorithm 48 stored in a memory subsystem of the processor-controlled device 300. One or more processors communicate with the memory subsystem and execute the cane-side algorithm 42 and the device-side algorithm 48. Because the processor-controlled device 300 illustrated in FIG. 27 is well-known to those of ordinary skill in the art, no detailed explanation is needed.

Figure 28:
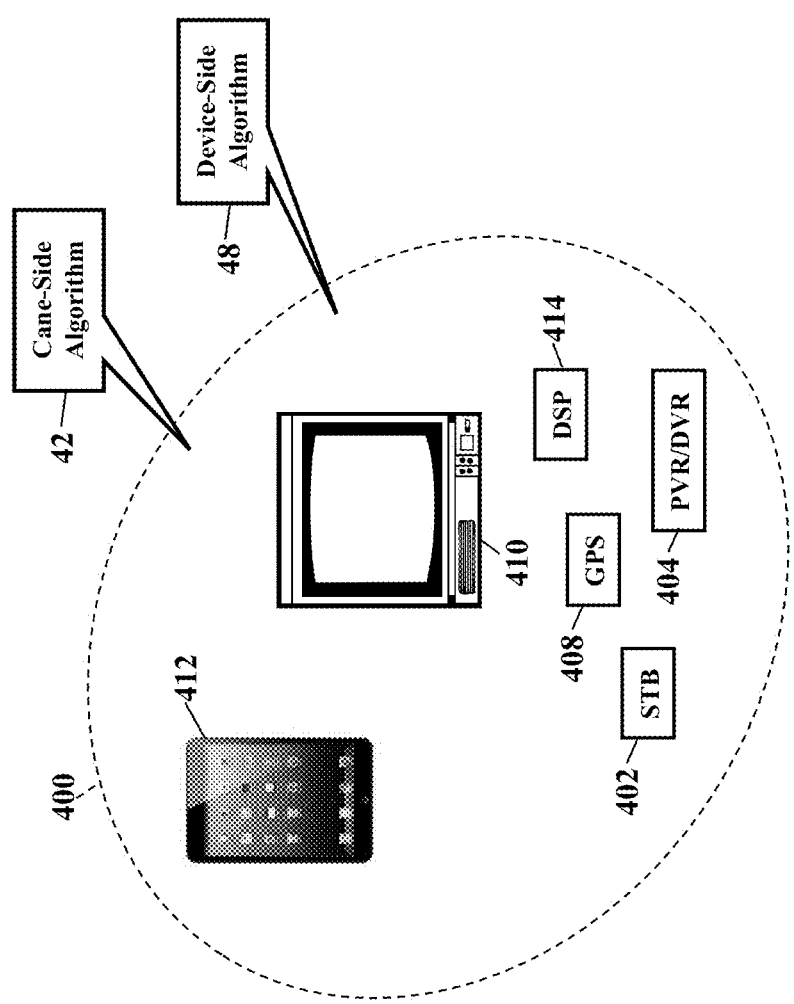

FIG. 28 depicts other possible operating environments for additional aspects of the exemplary embodiments. FIG. 28 illustrates the cane-side algorithm 42 and the device-side algorithm 48 operating within various other devices 400. FIG. 28, for example, illustrates that the cane-side algorithm 42 and/or the device-side algorithm 48 may entirely or partially operate within a set-top box ("STB") (402), a personal/digital video recorder (PVR/DVR) 404, a Global Positioning System (GPS) device 408, an interactive television 410, a tablet computer 412, or any computer system, communications device, or processor-controlled device utilizing the processor 50 and/or a digital signal processor (DP/DSP) 414. The device 400 may also include watches, radios, vehicle electronics, clocks, printers, gateways, mobile/implantable medical devices, and other apparatuses and systems. Because the architecture and operating principles of the various devices 400 are well known, the hardware and software componentry of the various devices 400 are not further shown and described.

Exemplary embodiments may be physically embodied on or in a computer-readable storage medium. This computer-readable medium may include CD-ROM, DVD, tape, cassette, floppy disk, memory card, and large-capacity disks. This computer-readable medium, or media, could be distributed to end-subscribers, licensees, and assignees. These types of computer-readable media, and other types not mention here but considered within the scope of the exemplary embodiments. A computer program product comprises processor-executable instructions for avoiding obstacles, as explained above.

While the exemplary embodiments have been described with respect to various features, aspects, and embodiments, those skilled and unskilled in the art will recognize the exemplary embodiments are not so limited. Other variations, modifications, and alternative embodiments may be made without departing from the spirit and scope of the exemplary embodiments.

The invention claimed is:
1. A method, comprising:
pairing a walking cane to a mobile smart phone;

receiving, by the mobile smart phone, a cane identifier during the pairing, the cane identifier uniquely identifying the walking cane;

querying, by the mobile smart phone, an electronic database for the cane identifier, the electronic database having electronic associations between parameters and cane identifiers including the cane identifier received during the pairing;

retrieving, by the mobile smart phone, a length of the walking cane from the electronic database, the length electronically associated with the cane identifier;

retrieving, by the mobile smart phone, an arm length from the electronic database, the arm length electronically associated with the cane identifier and describing a length of an arm of a visually impaired user of the mobile smart phone;

receiving, by the mobile smart phone, a command sent from the walking cane, the command instructing the mobile smart phone to activate a camera;

storing, by the mobile smart phone, an image of a tip of the walking cane;

receiving, by the mobile smart phone, an orientation angle associated with the walking cane; and inferring, by the mobile smart phone, a distance from the tip of the walking cane to the mobile smart phone, the distance based on information in the image, the orientation angle, the length of the walking cane, and the arm length, wherein the distance is used to aid the visually impaired user of the mobile smart phone.

2. The method of claim 1, further comprising:
calculating a first maximum for the distance from the tip of the walking cane to the mobile smart phone, the first maximum distance as twice the length of the walking cane; and
calculating a second maximum for the distance as a sum of the length of the walking cane and the arm length of the visually impaired user.

3. The method of claim 1, further comprising storing an association between the image of the tip of the walking cane and the orientation angle of the walking cane.

4. The method of claim 1, further comprising storing a database of images that associates different images of the tip of the walking cane to corresponding distances from the tip of the walking cane to the mobile smart phone.

5. The method of claim 4, further comprising comparing the image of the tip of the walking cane to images associated with the database of images.

6. The method of claim 5, further comprising selecting a matching image in the database of images that matches the image of the tip of the walking cane.

7. The method of claim 6, further comprising retrieving a corresponding distance that is associated with the matching image in the database of images.

8. The method of claim 7, further comprising using the corresponding distance associated with the matching image as the distance from the tip of the walking cane to the mobile smart phone.

9. A system, comprising:
a processor; and
a memory device, the memory device storing instructions, the instructions when executed causing the processor to perform operations, the operations comprising:
pairing a walking cane with a mobile smart phone;
receiving a cane identifier during the pairing, the cane identifier uniquely identifying the walking cane;
querying an electronic database for the cane identifier, the electronic database having electronic associations between parameters and cane identifiers including the cane identifier received during the pairing;
retrieving a length of the walking cane from the electronic database, the length electronically associated with the cane identifier;
retrieving an arm length from the electronic database, the arm length electronically associated with the cane identifier and describing a length of an arm of a visually impaired user of the mobile smart phone;
receiving a command sent from the walking cane, the command instructing the mobile smart phone to activate a camera;
storing an image of a tip of the walking cane in response to the command;
receiving an orientation angle associated with the walking cane; and
inferring a distance from the tip of the walking cane to the mobile smart phone based on information in the image, the orientation angle, the length of the walking cane, and the arm length of the walking cane,
wherein the distance is used to aid the visually impaired user of the mobile smart phone.

10. The system of claim 9, wherein the operations further comprise:
calculating a first maximum for the distance from the tip of the walking cane to the mobile smart phone, the first maximum distance as twice the length of the walking cane; and
calculating a second maximum for the distance as a sum of the length of the walking cane and the arm length of the visually impaired user.

11. The system of claim 9, further comprising storing an association between the image of the tip of the walking cane and the orientation angle of the walking cane.

12. The system of claim 9, wherein the operations further comprise storing a database of images that associates different images of the tip of the walking cane to corresponding distances from the tip of the walking cane to the mobile smart phone.

13. The system of claim 12, wherein the operations further comprise comparing the image of the tip of the walking cane to a database of images.

14. The system of claim 13, wherein the operations further comprise selecting a matching image in the database of images that matches the image of the tip of the walking cane captured by the camera.

15. The system of claim 14, wherein the operations further comprise retrieving a corresponding distance that is associated with the matching image in the database of images.

16. The system of claim 15, wherein the operations further comprise using the corresponding distance associated with the matching image as the distance from the tip of the walking cane to the mobile smart phone.

17. A memory device storing instructions that when execute cause a processor to perform operations, the operations comprising:
pairing a walking cane with a mobile smart phone;
receiving a cane identifier during the pairing, the cane identifier uniquely identifying the walking cane;
querying an electronic database for the cane identifier, the electronic database having electronic associations between parameters and cane identifiers including the cane identifier received during the pairing;

retrieving a length of the walking cane from the electronic database, the length electronically associated with the cane identifier;

retrieving an arm length from the electronic database, the arm length electronically associated with the cane identifier and describing a length of an arm of a visually impaired user of the mobile smart phone;

receiving a command sent from the walking cane, the command instructing the mobile smart phone to activate a camera;

storing an image of a tip of the walking cane in response to the command;

receiving an orientation angle associated with the walking cane; and inferring a distance from the tip of the walking cane to the mobile smart phone based on information in the image, the orientation angle, the length of the walking cane, and the arm length of the walking cane, wherein the distance is used to aid the visually impaired user of the mobile smart phone.

* * * * *